(12) United States Patent
Chye et al.

(10) Patent No.: US 10,968,463 B2
(45) Date of Patent: Apr. 6, 2021

(54) METHODS OF USING ACYL-COENZYMEA-BINDING PROTEINS TO ENHANCE TOLERANCE TO NECROTROPHIC FUNGAL PATHOGENS IN GENETICALLY MODIFIED PLANTS

(71) Applicant: The University of Hong Kong, Hong Kong (HK)

(72) Inventors: Mee Len Chye, Hong Kong (CN); Saritha Panthapulakkal Narayanan, Hong Kong (CN); Clive Sze Chung Lo, Hong Kong (CN); Pan Liao, Hong Kong (CN)

(73) Assignee: The University of Hong Kong, Hong Kong (HK)

( * ) Notice: Subject to any disclaimer, the term of this patent is extended or adjusted under 35 U.S.C. 154(b) by 0 days.

(21) Appl. No.: 16/313,375

(22) PCT Filed: Jul. 11, 2016

(86) PCT No.: PCT/CN2016/089677
§ 371 (c)(1),
(2) Date: Dec. 26, 2018

(87) PCT Pub. No.: WO2018/010075
PCT Pub. Date: Jan. 18, 2018

(65) Prior Publication Data
US 2019/0161769 A1    May 30, 2019

(51) Int. Cl.
*C12N 15/82* (2006.01)
*C07K 14/415* (2006.01)
*G01N 33/50* (2006.01)

(52) U.S. Cl.
CPC ........ *C12N 15/8282* (2013.01); *C07K 14/415* (2013.01); *G01N 33/5097* (2013.01)

(58) Field of Classification Search
None
See application file for complete search history.

(56) References Cited

U.S. PATENT DOCUMENTS 7,332,650 B2 * 2/2008 Ali ..................... C12N 15/8282
435/419

FOREIGN PATENT DOCUMENTS

CN          104946666    *  9/2015
WO     WO 2008113163    *  9/2008

OTHER PUBLICATIONS

Chen, et al., "Overexpression of the *Arabidopsis* 10-Kilodalton Acyl-Coenzyme A-Binding Protein ACBP6 Enhances Freezing Tolerance1," Plant Physiology 148(1):304-315 (2008).

(Continued)

*Primary Examiner* — Medina A Ibrahim
(74) *Attorney, Agent, or Firm* — Dentons US LLP

(57) ABSTRACT

OsACBP5 can be used to enhance tolerance to fungal necrotrophs in genetically modified plants. OsACBP5-overexpressing transgenic *Arabidopsis* were conferred enhanced tolerance to fungal necrotrophs such as root-infecting necrotroph *Rhizoctonia solani* and shoot-infecting necrotrophs (*Botrytis cinerea* and *Alternaria brassicicola*). Vectors/expression cassettes for conferring tolerance to fungal necrotrophs to plants/plant material are provided. Methods of using OsACBP5 to enhance tolerance to fungal necrotrophs are provided. Plants and plant material with improved tolerance to fungal necrotrophs are also provided. Methods for screening for genes with OsACBP5-like activity are also provided.

Figure 1:
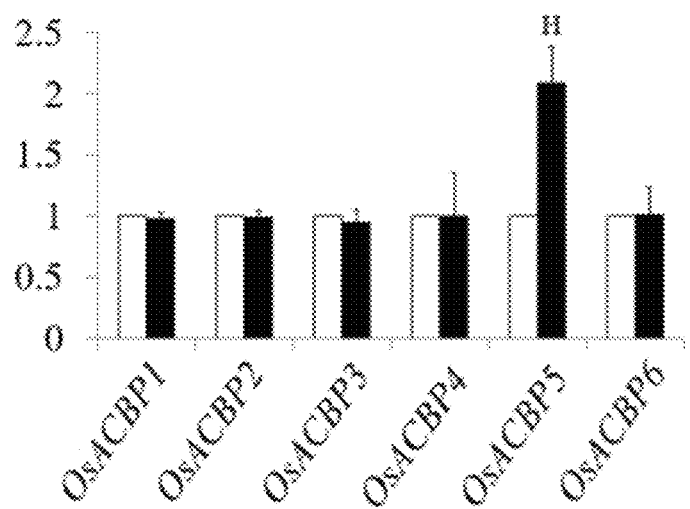

20 Claims, 6 Drawing Sheets
Specification includes a Sequence Listing.

(56) References Cited

OTHER PUBLICATIONS

Chye, et al., "Isolation of a Gene Encoding *Arabidopsis* Membrane-Associated Acyl-CoA Binding Protein and Immunolocalization of its Gene Product," Plant Journal 18(2):205-214 (1999).

Du, et al., "Depletion of the Membrane-Associated Acyl-Coenzyme A-Binding Protein ACBP1 Enhances the Ability of Cold Acclimation in *Arabidopsis*," Plant Physiology 152(3):1585-1597 (2010).

International Search Report and Writing Opinion regarding International Application No. PCT/CN2016/089677, dated Mar. 15, 2017.

Leung, et al., "ACBP4 and ACBP5, Novel *Arabidopsis* Acyl-CoA-Binding Proteins with Kelch Motifs that Bind Oleoyl-CoA," Plant Molecular Biology 55(2):297-309 (2004).

Leung, et al., "*Arabidopsis* ACBP3 Is an Extracellularly Targeted Acyl-CoA-Binding Protein," Planta 223(5):871-881 (2006).

Li and Chye, "*Arabidopsis* Acyl-CoA-Binnding Protein ACBP2 Interacts with an Ethylene-Responsive Element-Binding Protein, AtEBP, via its Ankyrin Repeats," Plant Molecular Biology 54(2):233-243 (2004).

Li and Chye, "Membrane Localization of *Arabidopsis* Acyl-CoA Binding Protein ACBP2," Plant Molecular Biology 51(4):483-492 (2003).

Meng, et al., "Rice Acyl-CoA-Binding Proteins OsACBP4 and OsACBP5 Are Differentially Localized in the Endoplasmic Reticulum of Transgenic *Arabidopsis*," Plant Signal Behav 9:e29544 (2014).

Meng, et al., "Subcellular Localization of Rice Acyl-CoA-Binding Proteins (ACBPs) Indicates that OsACBP6::GFP is Targeted to the Peroxisomes," New Phytol 203(2):469-482 (2014).

Meng, et al., "The Rice Acyl-CoA-Binding Protein Gene Family: Phylogeny, Expression and Functional Analysis," New Phytol 189(4):1170-1184 (2011).

Xiao and Chye, "New Roles for Acyl-CoA-Bilding Proteins (ACBPs) in Plant Development, Stress Responses and Lipid Metabolism," Progress in Lipid Research 50(2):141-151 (2011).

Xiao and Chye, "Overexpression of *Arabidopsis* ACBP3 Enhances NPR1-Dependent Plant Resistance to Pseudomonas syringe pv tomato DC3000," Plant Physiology 156(4):2069-2081 (2011).

Xiao, et al., "Overexpression of Membrane-Associated Acyl-CoA-Binding Protein ACBP1 Enhances Lead Tolerance in *Arabidopsis*," Plant Journal 54(1):141-151 (2008).

\* cited by examiner

METHODS OF USING ACYL-COENZYMEA-BINDING PROTEINS TO ENHANCE TOLERANCE TO NECROTROPHIC FUNGAL PATHOGENS IN GENETICALLY MODIFIED PLANTS

FIELD OF THE INVENTION

The present invention generally relates to the field of plant engineering. In particular, the present invention relates to genetically engineered plants that overexpress one or more rice ACYL-COENZYMEA-BINDING PROTEINS (OsACBP5) in an amount effective to enhance tolerance to fungal necrotrophs as well as methods of enhancing tolerance to fungal necrotrophs in genetically modified plants. In certain embodiments, the ACBP5 is OsACBP5.

CROSS REFERENCE TO RELATED APPLICATIONS

This application is a 371 National Stage application of International Application No. PCT/CN2016/089677, filed Jul. 11, 2016.

INCORPORATION OF SEQUENCE LISTING

A sequence listing contained in the file named "VRST005US-revised_ST25.txt" which is 10,956 bytes (measured in MS-Windows®) and was created on Oct. 11, 2019, is filed electronically herewith and incorporated by reference its entirety.

BACKGROUND OF THE INVENTION

Crops are susceptible to bacterial pathogens as well as eukaryotic pathogens including fungal pathogens. Fungal plant diseases are a significant concern in agriculture and food production worldwide. Necrotrophic soil-borne pathogenic fungi such as *Rhizoctonia* and *Fusarium* infect major economically-important crops leading to severe yield loss (www.bats.ch/bats/publikatioen/1995-1_TA/1-introduction-.php) (www.agrivi.com/yield-losses-due-to-pests/). For example, yield losses of 10-30% were commonly observed in pulse crops infected with severe root-rot caused by fungal necrotroph *Fusarium* species (Cichy et al., *Plant and soil,* 300:233-244 (2007)). Soybean foliar blight disease is caused by the fungal necrotroph *Rhizoctonia solani* AG-1 in Japan and the yield loss was estimated to be upto 70% (Narayanasamy, *Springer Science & Business Media* 16 (2013). The economic impact of necrotrophic pathogens on agriculture was highlighted by a recent survey (Murray and Brennan, *Australasian Plant Pathology,* 38:558-570 (2009)). The report indicated that the losses in wheat and barley in Australia resulting from tan spot and *Stagonospora nodorum* blotch, both of which are caused by necrotrophic pathogens, significantly exceeded losses resulting from wheat rusts and mildews, which are caused by biotrophic pathogens. In addition, the necrotroph *Botrytis cinerea* infects almost all vegetable and fruit crops and annually results in worldwide losses of $10 to $100 billion. To ensure a steady and uniform food supply to the rapidly mounting global population, there is an urgent need to control necrotrophic fungal diseases. To this end, proteins that can protect plants from necrotrophic phytopathogens must be identified and subsequently tested for efficacy in transgenic crops.

The acyl-CoA-binding proteins (ACBPs) represent a major group of proteins involved in lipid transfer in eukaryotes. The *Arabidopsis* ACBPs bind long-chain acyl-CoA esters and are implicated in plant development, growth and stress responses (Xiao and Chye, *Progress in Lipid Research,* 50:141-151 (2011)). Of the six *Arabidopsis* ACBPs, AtACBP3 expression was induced by biotrophic bacterial phytopathogen (*Pseudomonas syringae* pv tomato DC3000) and necrotrophic fungal pathogen (*Botrytis cinerea*) treatment in RNA gel-blot analyses and transgenic *Arabidopsis* AtACBP3-overexpressing (OE) lines were conferred protection against the biotrophic bacterial pathogen *Pseudomonas syringae* but not the necrotrophic fungal pathogen *Botrytis cinerea* (Xiao and Chye, *Plant Physiology,* 156:2069-2081, (2011)). Rice ACBP5 resembles AtACBP3 in being classified as a Class III ACBP with the acyl-CoA-binding (ACB) domain at the C-terminus unlike the other 4 Classes (Meng et al., *New Phytologist,* 189:1170-1184 (2011)). OsACBP5 mRNA expression in quantitative real-time PCR (qRT-PCR) analysis was reported to be upregulated after infection with the hemibiotrophic rice blast fungus *Magnaporthe grisea* (Meng et al., *New Phytologist,* 189:1170-1184 (2011)). However, tests on OsACBP5 expression after infection with the necrotrophic fungal pathogen have not been reported.

Plant pathogens are classified based on their modes of nutrition. Necrotrophic pathogens actively kill host tissue as they colonize and thrive on the contents of dead or dying cells (Lewis, *Biological Review,* 48:261-278 (1973)). This lifestyle contrasts with that of biotrophic pathogens which derive nutrients from living cells and therefore must maintain host viability (Lewis, *Biological Review,* 48:261-278 (1973)). A third group, the hemibiotrophs, display both forms of nutrient acquisition shifting from an early biotrophic phase to necrotrophy at later stages of disease. The duration of the biotrophic or necrotrophic phase varies significantly among hemibiotrophic pathogens (Perfect and Green, *Molecular Plant Pathology* 2:101-108 (2001)). Hence, necrotrophic pathogens render a more damaging effect on host plants compared with biotrophic pathogen and are deemed more threatening to crop productivity.

Thus, there is a need for genetically modified plants with enhanced protection against necrotrophic fungal pathogens and a method for producing the same. The present invention fulfills such a need.

SUMMARY OF THE INVENTION

In one embodiment, the present invention using transgenic *Arabidopsis* OsACBP5-OE lines showed that OsACBP5 conferred resistance not only to the prokaryotic bacterial biotroph *Pseudomonas syringae* but also to the eukaryotic fungal necrotrophs including the root-infecting necrotroph *Rhizoctonia solani,* and the shoot-infecting necrotrophs (*Botrytis cinerea* and *Alternaria brassicicola*). These findings suggest that although AtACBP3 and OsACBP5 belong to Class III ACBPs, OsACBP5 differs from AtACBP3 in providing protection to a wide range of necrotrophic fungal pathogens (*R. solani, B. cinerea* and *A. brassicicola*) that infects rice and other important global crops. This characteristic is unlike AtACBP3 because AtACBP3-OE lines were more susceptible to necrotrophic fungal pathogen.

In one embodiment, transgenic plants and plant material with improved tolerance to fungal necrotrophs are provided. It has been discovered that expressing *Oryza sativa* ACYL-COENZYMEA-BINDING PROTEINS (OsACBP5) in plants improves tolerance to fungal necrotrophs relative to unmodified plants. We can express OsACBP5 in crop plants to help them withstand fungal infection, for growing flowers, fruits, vegetables and other crops to enhance crop yield. In a further embodiment, the transformed plants are transgenic or transplastomic *Arabidopsis*, tomato, tobacco, cotton, corn, and rice plants. In one embodiment, tolerance to fungal necrotrophs in a plant can be measured by the ability to survive necrotrophic fungal infection.

In one embodiment, the present invention provides modified plants that comprise OsACBP5 polypeptides or variants thereof able to convey to the host organism tolerance to fungal necrotrophs. The present invention also provides a method of producing modified plants which comprises transforming a plant with a plastid and/or nuclear transformation vector comprising at least one OsACBP5-encoding polynucleotide.

In one embodiment, the invention provides plant transformation vectors for improving tolerance to fungal necrotrophs in plants, which include a nucleic acid sequence encoding an OsACBP5 polypeptide or a functional fragment or variant thereof. In some embodiments, the vectors comprise a promoter, operably linked to a sequence encoding an OsACBP5 polypeptide or a functional fragment or variant thereof, and a terminator, and/or other regulatory elements. The promoter can be constitutive, inducible or tissue specific. In other embodiments, the vector can be designed so that it will be expressed under the control of a plant's own endogenous promoter. The vectors may encode more than one OsACBP5 polypeptide or a functional fragment or variant thereof as an operon. The vectors described herein include plant plastid transformation vectors or nuclear transformation vectors.

Figure 3:
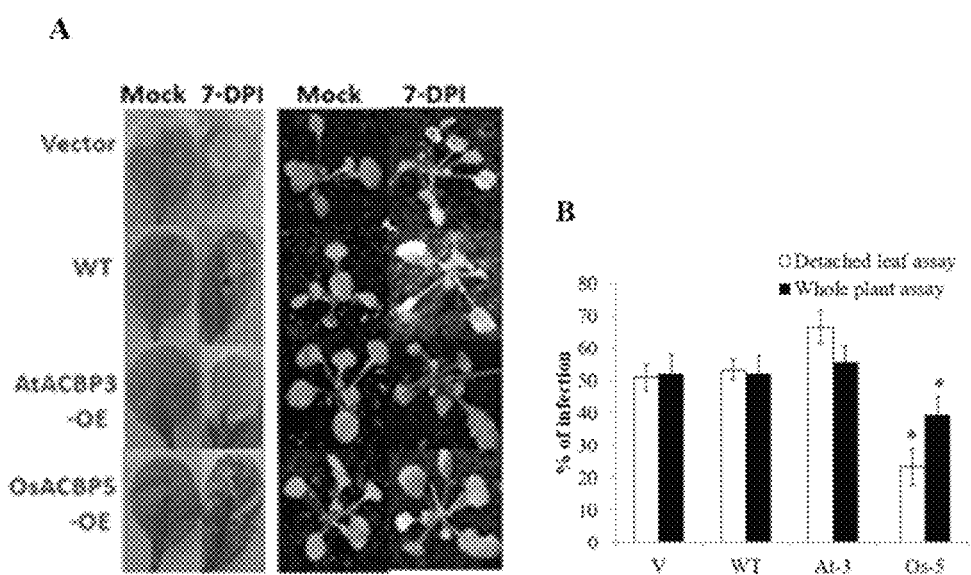

Also provided is a method of producing modified plants or plant cells with tolerance to fungal necrotrophs. The method includes transforming a plant or plant cell with the vectors described herein, which comprise an OsACBP5-encoding polynucleotide. In some embodiments, a nuclear transformation vector is used to cause expression of one or more OsACBP5s or variants thereof, conveying similar tolerance to fungal necrotrophs as the OsACBP5 polypeptides. In other embodiments, a plastid transformation vector is used to cause expression of one or more OsACBP5s or variants thereof conveying similar tolerance to fungal necrotrophs as the OsACBP5 polypeptides. Such nuclear and plastid transformation vectors can be used alone or in conjunction with each other or with other recombinant vectors that can enhance tolerance to fungal necrotrophs of plants transformed therewith.

Also provided is a method for screening for OsACBP5-like sequences or variants, which confer tolerance to fungal necrotrophs to plants. The method includes introducing an exogenous nucleic acid into a host cell which exhibits growth inhibition in fungal conditions, to form a test cell, where relief of growth inhibition indicates OsACBP5-like ability to confer growth tolerance. In some embodiments, the exogenous nucleic acid is mutated prior to being introduced into the host cell. In other embodiments, the exogenous nucleic acid is a synthetic nucleic acid encoding a variant of OsACBP5.

In an embodiment, the invention relates to a cell of a transgenic plant genetically engineered to express OsACBP5 in an amount effective to enhance tolerance to fungal necrotrophs relative to an unmodified plant.

In another embodiment, the invention relates to a method of obtaining enhanced tolerance to fungal necrotrophs in a plant or plant cell comprising: genetically engineering the plant or plant cell to express OsACBP5 in an amount effective to provide tolerance to fungal necrotrophs relative to a non-genetically engineered plant.

In another embodiment, the invention relates to a method of obtaining a plant part having tolerance to fungal necrotrophs, comprising: obtaining a plant part genetically modified to express OsACBP5; and growing the plant part under conditions where it is exposed to fungalstress sufficient to be growth-inhibiting to a native plant of the same type.

In another embodiment, the invention relates to a method of screening for functional OsACBP5 variants, comprising: obtaining a cell genetically modified to express a candidate OsACBP5 variant; growing the cell under conditions of fungal stress for a duration that is sufficient to be growth-inhibiting to a native cell of the same type; observing whether the cell exhibits a reduction in growth inhibition; and, if so, identifying the candidate OsACBP5 variant as functional.

In another embodiment, the invention relates to the use of a cell as described herein for the production of a plant tissue.

In another embodiment, the invention relates to the use of a cell as described herein for the production of a plant or plant part.

In another embodiment, the invention relates to the use of a plant comprising a cell as described herein for the production of progeny, seeds, or propagating material of the plant and of the progeny.

BRIEF DESCRIPTION OF THE DRAWINGS

FIG. 1 shows the expression of OsACBPs in 2-week-old wild-type *Oryza sativa* ssp. *Japonica* cv. Dongjin infected with the root-infecting necrotrophic fungal pathogen *Rhizoctonia solani* by quantitative real-time PCR. Total RNA was extracted from the 2-week-old wild-type rice seedlings. Open bars, mock; closed bars, 5 dpi, days post-inoculation. Expression was normalized to that of ActinI following Schmittgen and Livak, *Nat. Protoc.* 3:1101-1108, (2008). H, value higher than the control ($P<0.05$); L, value lower than the control ($P<0.05$).

FIGS. 2A and 2B show that OsACBP5-OEs can confer protection in *Arabidopsis* against shoot-infecting necrotrophic fungal pathogen *Botrytis cinerea* on *Arabidopsis* detached leaf and whole plant assays. FIG. 2A (left) shows the detached leaf assays on six-week-old *Arabidopsis* leaves of the vector-control (pBI-eGFP), *Arabidopsis* wild-type, transgenic *Arabidopsis* 35S::AtACBP3::GFP and 35S::OsACBP5::GFP lines inoculated with the necrotrophic fungal pathogen *Botrytis cinerea* following Ferrari et al., *Plant Physiology,* 144:367-379 (2007). FIG. 2A (right) shows the whole plant assays on four-week-old *Arabidopsis* seedlings of the vector-control (pBI-eGFP), *Arabidopsis* wild-type (WT), transgenic *Arabidopsis* 35S::AtACBP3::GFP and 35S::OsACBP5::GFP lines inoculated with the necrotrophic fungal pathogen *B. cinerea* following Xiao and Chye, *Plant Physiology.,* 156:2069-2081, (2011). The plants were photographed 7-days post-inoculation. FIG. 2B shows the infection by the necrotrophic fungus *B. cinerea* on wild-type (WT), transgenic *Arabidopsis* 35S::AtACBP3::GFP (At-3), 35S::OsACBP5::GFP (Os-5) and the vector control (V). *Significant decrease in % of infection ($P<0.05$). DPI, days post-inoculation.

FIGS. 3A and 3B show that OsACBP5-OEs can confer protection in *Arabidopsis* against shoot-infecting necrotrophic fungal pathogen *Alternaria brassicicola* on *Arabidopsis* detached leaf and whole plant assays. FIG. 3A (left) shows the detached leaf assays on six-week-old *Arabidopsis* leaves of the vector-control (pBI-eGFP), *Arabidopsis* wild-type, transgenic Arabidopsis 35S::AtACBP3::GFP and 35S::OsACBP5::GFP lines inoculated with the necrotrophic fungal pathogen A. brassicicola following Botanga et al., Molecular Plant-Microbe Interactions, 25:1628-1638 (2012). FIG. 3A (right) shows that whole plant assays on Arabidopsis four-week-old seedlings of the vector-control (pBI-eGFP), wild-type, 35S::AtACBP3::GFP and 35S::OsACBP5::GFP lines inoculated with the necrotrophic fungus A. brassicicola following Botanga et al., Molecular Plant-Microbe Interactions, 25:1628-1638 (2012). The Arabidopsis plants were photographed 7-days post-inoculation. FIG. 3B. shows the infection by the necrotrophic fungus A. brassicicola on wild-type (WT), transgenic Arabidopsis 35S::AtACBP3::GFP (At-3), 35S::OsACBP5::GFP (Os-5) and the vector control (V). *Significant decrease in % of infection (P<0.05). DPI, days post-inoculation.

Figure 4:
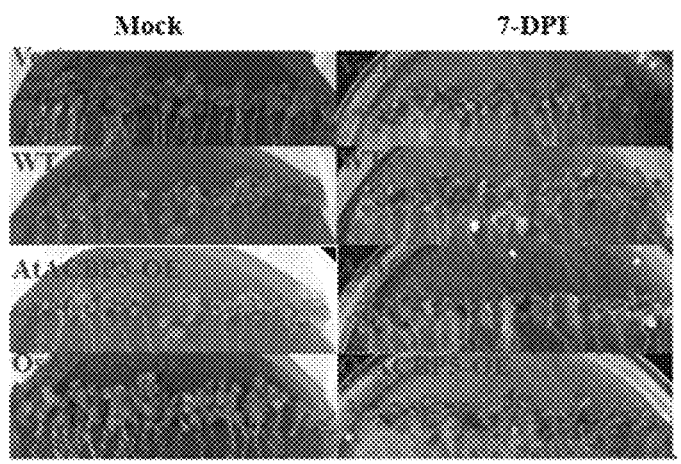
Figure 4:
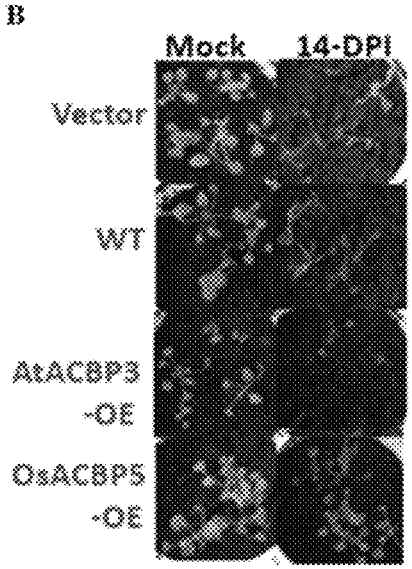
Figure 4:
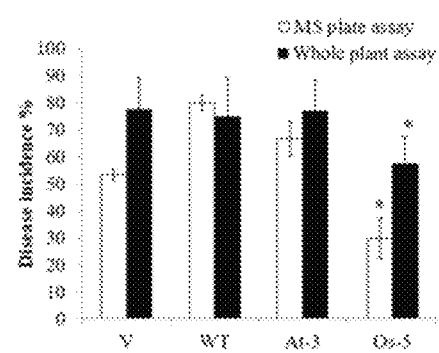

FIGS. 4A, 4B and 4C show that OsACBP5-OEs can confer protection in Arabidopsis against root-infecting necrotrophic fungal pathogen Rhizoctonia solanion Murashige and Skoog (MS) plate and whole plant assays. FIG. 4A shows the MS plate assays on one-week-old Arabidopsis seedlings of the vector-control (pBI-eGFP), Arabidopsis wild-type, transgenic Arabidopsis 35S::AtACBP3::GFP and 35S::OsACBP5::GFP lines infected with the necrotrophic fungal pathogen R. solani AG-1 following Perl-Treves et al., Molecular Plant-Microbe Interactions, 17:70-80 (2004). Photography was carried out at 7-days post inoculation. FIG. 4B shows the whole plant assays on one-week-old Arabidopsis seedlings of the vector-control (pBI-eGFP), Arabidopsis wild-type, transgenic Arabidopsis 35S::AtACBP3::GFP and 35S::OsACBP5::GFP lines inoculated with the necrotrophic fungus R. solani following Perl-Treves et al., Molecular Plant-Microbe Interactions, 17:70-80 (2004). Photography was carried out at 14-days post-inoculation. FIG. 4C shows the infection by the necrotrophic fungus R. solanion wild-type (WT), transgenic Arabidopsis 35S::AtACBP3::GFP (At-3), 35S::OsACBP5::GFP (Os-5) and the vector control (V). *Significant decrease in % of infection (P<0.05). DPI, days post-inoculation.

Figure 5:
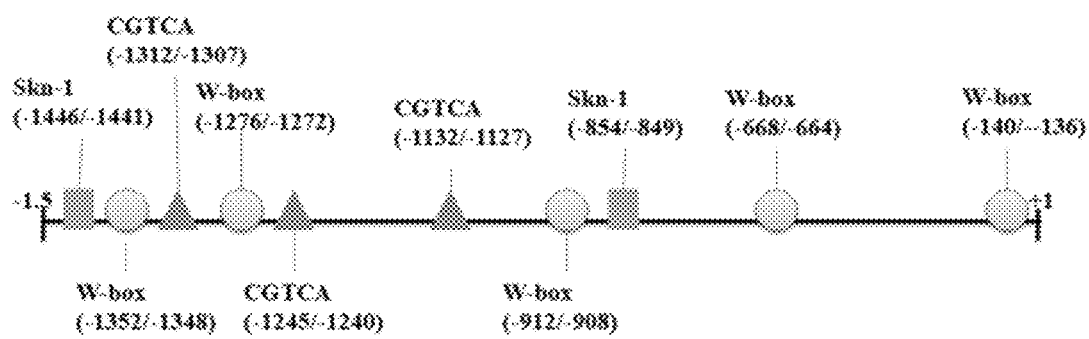
Figure 5:

FIGS. 5A, 5B and 5C show the electrophoretic mobility shift assay (EMSA) on the W-box (−1352/−1348). These assays were carried out following Zheng et al., Journal of Experimental Botany, 63:2985-3000 (2012). FIG. 5A shows putative elements in the 5'-flanking region of OsACBP5. FIG. 5B shows the nucleotide sequence of double-stranded oligonucleotide probe (ML2580 and ML2581) for the W-box. FIG. 5C shows the EMSA of the W-box. Lane 1, biotin labeled probe; lane 2, labeled probe and the necrotrophic fungus Rhizoctonia solani treated leaf nuclear extract; lane 3, labeled and unlabeled probe with the necrotrophic fungus R. solani treated leaf nuclear extract (competitor); lane 4, labeled probe and untreated leaf nuclear extract; and lane 5, labeled and unlabeled probe with untreated leaf nuclear extract (competitor). The protein-DNA complex is indicated by an arrow. I, pathogen treated wild-type rice leaf nuclear extract; U, untreated leaf nuclear extract.

Figure 6:
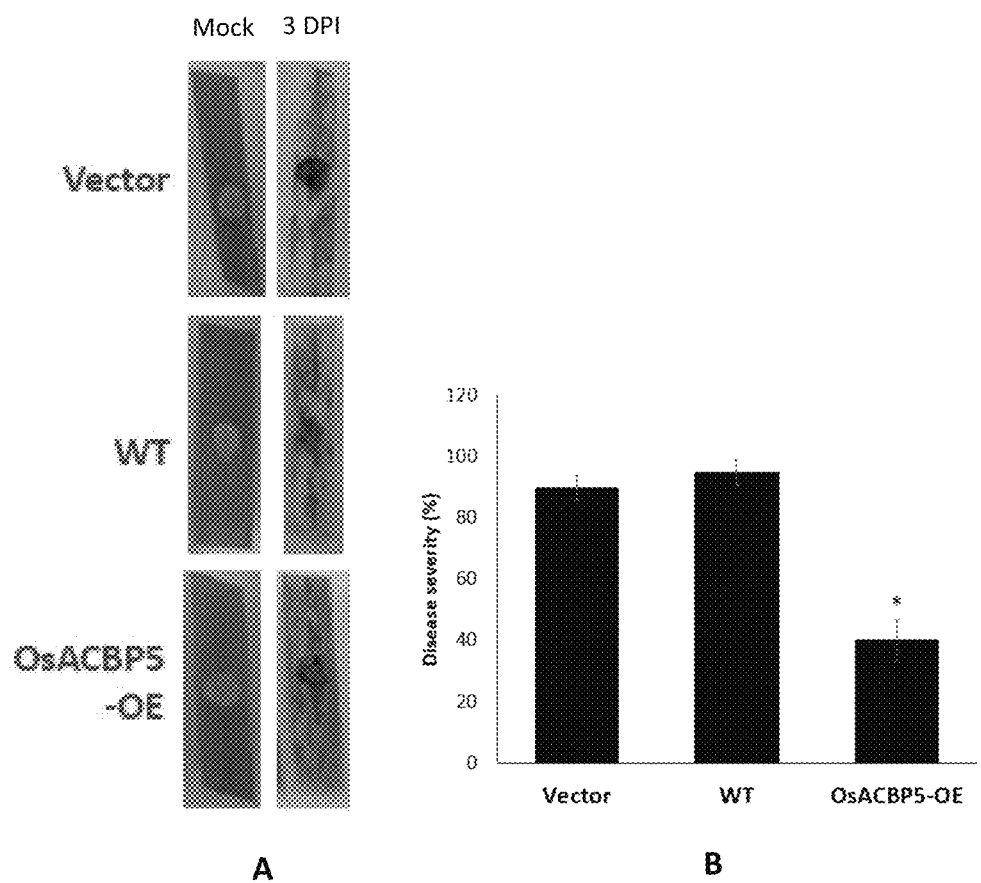

Table 1 shows the novel biotic stress-related proteins significantly unregulated in OsACBP5-overexpressors infected with the necrotrophic fungal pathogen Rhizoctonia solani FIGS. 6A and 6B show that transgenic OsACBP5-overexpressing rice is conferred protection against the root-infecting necrotrophic fungal pathogen Rhizoctonia solani in detached leaf assays. FIG. 6A shows the detached leaf assays on 8-week-old leaves from transgenic rice expressing the vector transformed-control (pCAMBIA1304) (vector), wild-type rice Zhonghua 11 (Oryza sativa L. subsp. japonica, ZH11) (WT) and transgenic rice 35S::OsACBP5-OE(OsACBP5-OE) line infected with the necrotrophic fungal pathogen R. solani AG-1 following Guleria et al., Journal of Phytopathology, 155:654-661 (2007). Photography was carried out at 3-days post inoculation. FIG. 6B shows the infection by the necrotrophic fungus R. solanion the vector, WT and OsACBP5-OE. *Significant decrease in % of infection (P<0.05). DPI, days post-inoculation.

DETAILED DESCRIPTION OF THE INVENTION

Genetically modified plants and progeny thereof expressing the acyl-CoA-binding protein, OsACBP5, exemplified herein by the Oryza sativa ACBP5 protein, exhibit improved tolerance to fungal necrotrophs as compared to non-modified plants.

Thus, the overexpression of OsACBP5 polypeptide in crop plants can help improvement of crop productivity and reduced use of fungicides.

The present invention provides a transgenic plant, seed and progeny thereof genetically engineered to overexpress one or more OsACBP5 in an amount effective to enhance tolerance to fungal necrotrophs as compared to a vector (pBI121-eGFP) transformed control plant. The present invention also provides a method of enhancing tolerance to fungal necrotrophs. Such method comprises genetically engineering a plant to overexpress one or more OsACBP5 in an amount effective to enhance resistance to fungal necrotrophs relative to a vector-transformed control plant.

"OsACBP5" is used herein to mean Oryza sativa acyl-coenzymeA-binding protein 5 and functional variants thereof (polynucleotides or polypeptides, as indicated by the context) that can convey improved tolerance to fungal necrotrophs example, tolerance to fungal necrotrophs in a plant can be measured by the ability to survive fungal infection.

"OsACBP5-OEs" is used herein to mean transgenic Arabidopsis thaliana overexpressing OsACBP5 polypeptide.

"OsACBP5-like polypeptide" as used herein includes polypeptides sharing at least 77% sequence identity to OsACBP5 that convey improved tolerance to fungal necrotrophs to the host cell, including variants of OsACBP5 described below.

OsACBP5-like polypeptide, OsACBP5 variants and OsACBP5 homologs as used herein refer to polypeptides, which like OsACBP5, can down regulate the negative "Chemically synthesized," as related to a sequence of DNA, means that the component nucleotides were assembled in vitro.

"Construct" as used herein refers to a recombinant nucleic acid, generally of a specific nucleotide sequence(s), or is to be used in the construction of other recombinant nucleotide sequences.

"DNA regulatory sequences," "control elements," and "regulatory elements," are used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

"Endogenous nucleic acid" as used herein refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Exogenous nucleic acid" as used herein refers to a nucleic acid that is not normally or naturally found in and/or produced by a given bacterium, organism, or cell in nature.

"Heterologous nucleic acid," as used herein, refers to a nucleic acid wherein at least one of the following is true: (a) the nucleic acid is foreign ("exogenous" i.e., not naturally found in) a given host microorganism or host cell; (b) the nucleic acid comprises a nucleotide sequence that is naturally found in e.g., is "endogenous to" a given host microorganism or host cell (e.g., the nucleic acid comprises a nucleotide sequence endogenous to the host microorganism or host cell); however, in the context of a heterologous nucleic acid, the same nucleotide sequence as found endogenously is produced in an unnatural (e.g., greater than expected or greater than naturally found) amount in the cell, or a nucleic acid comprising a nucleotide sequence that differs in sequence from the endogenous nucleotide sequence but encodes the same protein (having the same or substantially the same amino acid sequence) as found endogenously is produced in an unnatural (e.g., greater than expected or greater than naturally found) amount in the cell; (c) the nucleic acid comprises two or more nucleotide sequences that are not found in the same relationship to each other in nature, e.g., the nucleic acid is recombinant. An example of a heterologous nucleic acid is a nucleotide sequence encoding an OsACBP5 operably linked to a transcriptional control element (for example, a promoter) to which an endogenous (naturally-occurring) OsACBP5 coding sequence is not normally operably linked. Another example of a heterologous nucleic acid is a high copy number plasmid comprising a nucleotide sequence encoding an OsACBP5.

Another example of a heterologous nucleic acid is a nucleic acid encoding an OsACBP5, where a host cell that does not normally produce OsACBP5 is genetically modified with the nucleic acid encoding OsACBP5; because OsACBP5-encoding nucleic acids are not naturally found in the host cell, the nucleic acid is heterologous to the genetically modified host cell.

"Host cell," as used herein, denotes an in vivo or in vitro eukaryotic cell, a prokaryotic cell, or a cell from a multicellular organism (for example, a cell line) cultured as a unicellular entity, which eukaryotic or prokaryotic cells can be, or have been, used as recipients for a nucleic acid (for example, an expression vector that comprises a nucleotide sequence encoding one or more gene products such as ACBPs), and includes the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation.

A "recombinant host cell" (also referred to as a "genetically modified host cell") is a host cell into which has been introduced a heterologous nucleic acid, e.g., an expression vector.

"Isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

"Naturally-occurring" or "native" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring, and "wild-type" plants are naturally occurring.

"Modified plant or plant parts" as used herein refers to a plant or plant part, whether it is attached or detached from the whole plant. It also includes progeny of the modified plant or plant parts that are produced through sexual or asexual reproduction.

"Operably linked" refers to a juxtaposition wherein the components so described are in a relationship permitting them to function in their intended manner. For instance, a promoter is operably linked to a coding sequence if the promoter affects its transcription or expression.

"Operon" and "single transcription unit" are used herein interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

"Peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

Percent "sequence identity" of a polypeptide or polynucleotide to another polynucleotide or polypeptide, meaning that, when aligned, that percentage of bases or amino acids are the same, and in the same relative position, when comparing the two sequences.

"Plant cell culture" refers to cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

"Plant tissue" refers to a group of plant cells organized into a structural and functional unit. Any tissue of a plant, whether in a plant or in culture, is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

"Polynucleotide" and "nucleic acid," are used interchangeably herein, and refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

"Progeny" includes the immediate and all subsequent generations of offspring traceable to a parent.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system.

Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Thus, for example, the term "recombinant" polynucleotide or nucleic acid refers to one which is not naturally occurring, for example, is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site.

Alternatively, it is performed to join together nucleic acid segments of desired functions to generate a desired combination of functions.

"Transformation" or "transformed" are used interchangeably herein with "genetic modification" or "genetically modified" and refer to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell or into a plastome of the cell. In prokaryotic cells, permanent changes can be introduced into the chromosome or via extrachromosomal elements such as plasmids, plastids, and expression vectors, which may contain one or more selectable markers to aid in their maintenance in the recombinant host cell.

"Transformation vectors and "expression cassettes" are used herein interchangeably.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene.

"Variant" as used herein refers either to a naturally occurring genetic mutant of OsACBP5 or a recombinantly prepared variation of OsACBP5, each of which contain one or more mutations in its DNA. The term "variant" may also refer to either a naturally occurring variation of a given peptide or a recombinantly prepared variation of a given peptide or protein in which one or more amino acid residues have been modified by amino acid substitution, addition, or deletion.

As used herein, the term "a control plant" refers to a vector (pBI121-eGFP)-transformed control plant, wherein the OsACBP5 polypeptide is not overexpressed.

Vectors/Expression Cassettes for Conferring Fungal Resistance

In *Arabidopsis*, a total of six forms of acyl-coenzymeA-binding proteins (ACBPs) have been identified and designated as AtACBP1 to AtACBP6 (Xiao et al., *Plant Journal*, 54:141-151 (2008)), ranging from 10 to 73.1 kD (Leung et al., *Plant Molecular Biology*, 55:297-309 (2004)). Membrane-associated AtACBP1 and AtACBP2 are subcellularly localized to the ER and plasma membrane (Chye et al., *Plant Journal*, 18:205-214 (1999); Li and Chye, *Plant Molecular Biology*, 51:483-492 (2003)), AtACBP3 is extracellularly-targeted (Leung et al., *Planta*, 223:871-881 (2006)) and kelch-motif-containing AtACBP4 and AtACBP5 (Leung et al., *Plant Molecular Biology*, 55:297-309 (2004)), as well as AtACBP6 are localized in the cytosol (Chen et al., *Plant Physiology*, 148: 304-315, 2008). Domains that potentially mediate protein-protein interactions, ankyrin repeats (AtACBP1 and AtACBP2) and kelch motifs (AtACBP4 and AtACBP5) (Leung et al., *Plant Molecular Biology*, 55: 297-309, 2004; Li and Chye, *Plant Molecular Biology*, 54: 233-243, 2004), are evident in the larger AtACBPs.

*Arabidopsis* ACBPs have been implicated in various stress responses, such as freezing (Chen et al., *Plant Physiology*, 148:304-315 (2008); Du et al., *Plant Physiology*, 152:1585-1597 (2010)) and pathogen resistance (Xiao and Chye, *Plant Physiology*, 156:2069-2081 (2011)).

Similar to *Arabidopsis*, rice ACBP family also contains six members, OsACBP1 to OsACBP6. The OsACBP1, OsACBP2 and OsACBP3 are grouped into Class I; OsACBP4 in Class II; OsACBP5 in Class III; and OsACBP6 in Class IV ACBPs (Meng et al., *New Phytologist*, 189:1170-1184 (2011). The OsACBP5 is unique from all other rice ACBPs as its ACB domain is located at the C-terminal segment, while, that of OsACBP1, OsACBP2, OsACBP3, OsACBP4 and OsACBP6 is located at the N-terminal segment (Meng et al., *New Phytologist*, 189: 1170-1184 (2011). The transgenic plants with OsACBP4 and OsACBP5 showed induced expression upon drought and high saline treatment. Among the rice ACBP family, only the expression of OsACBP5 was induced upon infection caused by the rice blast fungus *Magnaporthe grisea* (Meng et al., 2011). Interestingly, AtACBP3 and OsACBP5 belonging to Class III ACBP family share similar properties (Meng et al., 2011).

The Examples described herein show that the overexpression of OsACBP5 confers tolerance to fungal necrotrophs in plants.

The plant transformation vectors/expression cassettes provided herein include a nucleic acid sequence encoding an OsACBP5 polypeptide or a functional variant of OsACBP5 thereof. The vector can optionally also include a promoter, operably linked to the coding sequence, and a terminator, and/or other regulatory elements. The plant transformation vectors preferably include a transcription initiation or transcriptional control region(s) the coding region for the protein of interest, and a transcriptional termination region.

In one embodiment, the construct comprises operatively linked in the 5' to 3' direction, a promoter; one or more nucleic acid sequence encoding an OsACBP5 or a functional variant or fragment of OsACBP5; and a 3' polyadenylation signal.

In another embodiment, where the construct comprises more than one OsACBP5 or a functional variant of OsACBP5 thereof expressed as an operon, the nucleotide sequences can be operably linked to the same promoter. Alternatively, the nucleotide sequences may be under the control of different promoters.

Several plant transformation vector options are available, including those described in "Gene Transfer to Plants" (Potrykus, et al., eds.) Springer-Verlag Berlin Heidelberg New York (1995); "Transgenic Plants: A Production System for Industrial and Pharmaceutical Proteins" (Owen, et al., eds.) John Wiley & Sons Ltd. England (1996); and "Methods in Plant Molecular Biology: A Laboratory Course Manual" (Maliga, et al. eds.) Cold Spring Laboratory Press, New York (1995). Plant transformation vectors generally include one or more coding sequences of interest under the transcriptional control of 5' and 3' regulatory sequences, including a promoter, a transcription termination and/or polyadenylation signal, and a selectable or screenable marker gene. For the expression of two or more polypeptides from a single transcript, additional RNA processing signals and ribozyme sequences can be engineered into the construct (U.S. Pat. No. 5,519,164). This approach has the advantage of locating multiple transgenes in a single locus, which is advantageous in subsequent plant breeding efforts.

For direct expression of transgenes from the plastid genome, a vector to transform the plant plastid chromosome by homologous recombination is used in which case it is possible to take advantage of the prokaryotic nature of the plastid genome and insert a number of transgenes as an operon. Examples are described in U.S. Pat. No. 5,545,818 to McBride et al. WO 2010/061186 describes an alternative method for introducing genes into the plastid chromosome using an adapted endogenous cellular process for the transfer of RNAs from the cytoplasm to the plastid where they are incorporated by homologous recombination. This plastid transformation procedure is also suitable for practicing the disclosed compositions and methods.

A. OsACBP5

OsACBP5 genes useful in the vectors described herein include naturally occurring OsACBP5. Naturally occurring OsACBP5 is known in the art. An OsACBP5 sequence is found in the GenBank/EMBL data library under accession numbers ABF94919.1. Other genes useful for conferring fungal resistance to plants include variants of OsACBP5. In some embodiments, the variant is a synthetic nucleic acid. Preferably, the variants include less than 25, less than 20, less than 15, less than 10, less than 5, less than 4, less than 3, or less than 2 amino acid substitutions, rearrangements, insertions, and/or deletions relative to OsACBP5. In this regard, the term "variant" can encompass fragments, derivatives, and homologs of OsACBP5. The OsACBP5 homolog is preferably an OsACBP5-like sequence with at least 77% DNA homology to OsACBP5 and is capable of upregulating cell wall proteins (FLA10, LRX4, LRX5, XTH4, PME18), proteins involved in secondary metabolism (ESM1, Myrosinase1, Myrosinase2, NIT1) and jasmonic acid synthesis protein (AOC2) upon pathogen infection. More preferably, the variants include peptide sequences having at least 90% amino acid sequence identity to OsACBP5.

Sequence similarity can be determined using methods known in the art. For example, determine sequence identity, sequences can be aligned using the methods and computer programs, including BLAST, available over the world wide web at ncbi.nlm.nih.gov/BLAST. See, e.g., Altschul, et al. *Journal of Molecular Biology* 215:403-410 (1990). Another alignment algorithm is FASTA, available in the Genetics Computing Group (GCG) package, from Madison, Wis., USA, a wholly owned subsidiary of Oxford Molecular Group, Inc. Other techniques for alignment are described in *Methods in Enzymology*, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. *Methods in Molecular Biology*, 70: 173-187 (1997). Also, the GAP program using the Needleman and Wunsch alignment method can be utilized to align sequences. *Journal of Molecular Biology*, 48: 443-453 (1970).

In other embodiments, the variant of OsACBP5 is a mutant, isolated from a host cell as described herein. In still other embodiments, a variant OsACBP5 is encoded by a nucleic acid that hybridizes under stringent conditions to a nucleic acid encoding an *Oryza sativa* ACBP5 or another known OsACBP5.

B. Promoters

The selection of the promoter used in expression vectors determines the spatial and temporal expression pattern of the transgene in the transgenic plant. Promoters vary in their strength, i.e., ability to promote transcription. Selected promoters express transgenes in specific cell types (such as leaf epidermal cells, mesophyll cells, root cortex cells) or in specific tissues or organs (roots, leaves or flowers, for example) and the selection reflects the desired location of accumulation of the gene product. Alternatively, the selected promoter drives expression of the gene under various inducing conditions.

Various types of plant expressible promoters are suitable for the present invention, such as constitutive promoters, tissue-specific promoters and inducible promoters.

1. Constitutive Promoters

Suitable constitutive promoters for nuclear-encoded expression include, for example, the core promoter of the Rsyn7 promoter and other constitutive promoters disclosed in U.S. Pat. No. 6,072,050; the core CAMV 35S promoter, (Odell et al., *Nature* 313:810-812 (1985)); rice actin (McElroy et al., *Plant Cell* 2:163-171 (1990)); ubiquitin (Christensen et al., *Plant Molecular Biology*, 12:619-(1989) and Christensen et al., *Plant Molecular Biology*, 18:675-689 (1992)); pEMU (Last et al., *Theoretical and Applied Genetics* 81:581-588 (1991)); MAS (Yellen, et al., *EMBO J.*, 3:2723-2730 (1984)); and ALS promoter (U.S. Pat. No. 5,659,026). Other constitutive promoters include, for example, U.S. Pat. Nos. 5,608,149; 5,608,144; 5,604,121; 5,569,597; 5,466,785; 5,399,680; 5,268,463; 5,608,142.

2. Tissue Specific Promoters

"Tissue-preferred" promoters can be used to target a gene expression within a particular tissue such as seed, leaf or root tissue. Tissue-preferred promoters are described in Yamamoto et al., *Plant Journal* 12(2)255-265 (1997); Kawamata et al., *Plant Cell Physiology* 38(7):792-803 (1997); Hansen et al., *Molecular and General Genetics* 254(3):337-343 (1997); Russell et al., *Transgenic Research*. 6(2):157-168 (1997); Rinehart et al., *Plant Physiology*. 112(3):1331-1341 (1996); Van Camp et al., *Plant Physiology* 112(2):525-535 (1996); Canevascini et al., *Plant Physiology* 112(2):513-524 (1996); Yamamoto et al., *Plant Cell Physiology* 35(5):773-778 (1994); *Lam, Results Probl. Cell Differ.* 20:181-196 (1994); Orozco, et al., *Plant Molecular*

*Biology* 23(6):1129-1138 (1993); Matsuoka, et al., *Proc Natl. Acad. Sci. USA* 90(20):9586-9590 (1993); and Guevara-Garcia, et al., *Plant J.* (3):495-505 (1993). Suitable tissue specific expression patterns include green tissue specific, root specific, stem specific, and flower specific.

Promoters suitable for expression in green tissue include many which regulate genes involved in photosynthesis, and many of these have been cloned from both monocotyledons and dicotyledons. Leaf-specific promoters are known in the art. See, for example, Yamamoto, et al., *Plant J.* 12(2):255-265 (1997); Kwon, et al., *Plant Physiol.* 105:357-67 (1994); Yamamoto, et al. *Plant Cell Physiol.* 35(5):773-778 (1994); Gotor, et al. *Plant J.* 3:509-18 (1993); Orozco, et al., *Plant Mol. Biol.* 23(6):1129-1138 (1993); and Matsuoka, et al. *Proc. Natl. Acad. Sci. USA* 90(20):9586-9590 (1993). Another example is the maize PEPC promoter from the phosphoenol carboxylase gene (Hudspeth & Grula, *Plant Molec. Biol.* 12: 579-589 (1989)), and promoters include those encoding rbsC (Coruzzi et al., *EMBO J.*, 3:1671-1697 (1984)).

Root-preferred promoters are known and may be selected from the many available from the literature or isolated de novo from various compatible species.

See, for example, Hire et al. *Plant Mol. Biol.* 20(2): 207-218 (1992)(soybean root-specific glutamine synthetase gene); Keller and Baumgartner, *Plant Cell*, 3(10):1051-1061 (1991) (root-specific control element in the GRP 1.8 gene of French bean); Sanger et al., *Plant Mol. Biol.* 14(3):433-443 (1990) (root-specific promoter of the mannopine synthase (MAS) gene of *Agrobacterium tumefaciens*); and Miao et al., *Plant Cell*, 3(1):1 1'-22 (1991) (full-length cDNA clone encoding cytosolic glutamine synthetase (GS), which is expressed in roots and root nodules of soybean). See also U.S. Pat. Nos. 5,837,876; 5,750,386; 5,633,363; 5,459,252; 5,401,836; 5,110,732; 5,023,179 and 7,285,656. A suitable promoter for root specific expression is that described by de Framond *FEBS* 290: 103-106 (1991); EP 0 452 269 to de Framond and a root-specific promoter is that from the T-1 gene. SAHH or SHMT (Sivanandan et al., *Biochimica et Biophysica Acta*, 1731:202-208, 2005) is specific for root-specific expression. Also, the Cauliflower Mosaic Virus (CaMV) 35S promoter has been reported to have root-specific and leaf-specific modules in its promoter region (Benfey et al., *EMBO J.*, 8:2195-2202, 1989). Other tissue-specific promoters are well known and widely available to those of ordinary skill in the art.

A suitable stem specific promoter is that described in U.S. Pat. No. 5,625,136 and which drives expression of the maize trpA gene. Plastid specific promoters include the PrbcL promoter [Allison, et al., *EMBO J.* 15:2802-2809 (1996); Shiina, et al., *Plant Cell*, 10: 1713-1722 (1998)]; the PpsbA promoter [Agrawal, et al., *Nucleic Acids Research*, 29: 1835-1843 (2001)]; the Prm 16 promoter [Svab & Maliga, *Proc. Natl. Acad. Sci. USA* 90: 913-917 (1993), Allison, et al., *EMBO J.* 15: 2802-2809 (1996)]; the PaccD promoter (W097/06250; Hajdukiewicz, et al., *EMBO J.* 16: 4041-4048 (1997)).

3. Inducible Promoters

Inducible promoters, for example, chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Further, a wide variety of inducible promoters are also well known and widely available to those of ordinary skill in the art. Inducible promoter systems used successfully in plants have been extensively reviewed (Padidam, *Curr. Opin. Plant Biol.* 6:169 (2003); Wang, et al. *Trans. Res.*:12, 529 (2003); Gatz and Lenk, *Trends Plant Sci.* 3:352 (1998)).

These inducible systems may be activated by chemicals such as tetracycline, pristamycin, pathogen, light, glucocorticoid, estrogen, copper, herbicide safener, ethanol, IPTG (iso-propylil-D-1-thiogalactopyranoside), and pathogens.

Useful Chemical-inducible promoters and include, but are not limited to, the maize ln2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid. Other chemical-regulated promoters of interest include steroid-responsive promoters (see, for example, the glucocorticoid-inducible promoter in Schena, et al. *Proc. Natl. Acad. Sci. USA*, 88:10421-10425 (1991) and MeNellis, et al. *Plant J.*, 14(2):247-257 (1998)) and tetracycline-inducible and tetracycline-repressible promoters (see, for example, Gatz, et al., *MoL Gen. Genet.* 227:229-237 (1991), and U.S. Pat. Nos. 5,814,618 and 5,789,156).

Another suitable category of inducible promoters is that which is wound inducible. Numerous promoters have been described which are expressed at wound sites. Preferred promoters of this kind include those described by Stanford, et al., *MoL Gen. Genet.* 215:200-208 (1989), Xu, et al., *Plant Molec. Biol.*, 22: 573-588 (1993), Logemann, et al., *Plant Cell*, 1: 151-158 (1989), Rohrmeier & Lehle, *Plant Molec. Biol.*, 22: 783-792 (1993), Firek, et al., *Plant Molec. Biol.*, 22: 129-142 (1993), and Warner, et al., *Plant J.*, 3: 191-201 (1993).

C. Transcriptional Terminators

A variety of transcriptional terminators are available for use in expression cassettes. These are responsible for the termination of transcription beyond the transgene and its correct polyadenylation. Accordingly, at the extreme 3' end of the transcript of the transgene, a polyadenylation signal can be engineered. A polyadenylation signal refers to any sequence that can result in polyadenylation of the mRNA in the nucleus prior to export of the mRNA to the cytosol, such as the 3' region of nopaline synthase (Bevan, et al. *Nucleic Acids Res.*, 11:369-385 (1983). Other transcriptional terminators are those that are known to function in plants and include the CaMV 35S terminator, the tml terminator, the nopaline synthase terminator and the pea rbcS E9 terminator. These are used in both monocotyledonous and dicotyledonous plants.

D. Sequences for the Enhancement or Regulation of Expression

Numerous sequences have been found to enhance gene expression from within the transcriptional unit and these sequences can be used in conjunction with the genes to increase their expression in transgenic plants. For example, various intron sequences such as introns of the maize Adhl gene have been shown to enhance expression, particularly in monocotyledonous cells. In addition, a number of non-translated leader sequences derived from viruses are also known to enhance expression, and these are particularly effective in dicotyledonous cells.

E. Targeting Sequences

The disclosed vectors may further include, within the region that encodes the protein to be expressed, one or more nucleotide sequences encoding a targeting sequence. A "targeting" sequence is a nucleotide sequence that encodes an amino acid sequence or motif that directs the encoded protein to a particular cellular compartment, resulting in localization or compartmentalization of the protein. Presence of a targeting amino acid sequence in a protein typically results in translocation of all or part of the targeted protein across an organelle membrane and into the organelle interior.

Alternatively, the targeting peptide may direct the targeted protein to remain embedded in the organelle membrane. The "targeting" sequence or region of a targeted protein may contain a string of contiguous amino acids or a group of noncontiguous amino acids. The targeting sequence can be selected to direct the targeted protein to a plant organelle such as a nucleus, a microbody (e.g., a peroxisome, or a specialized version thereof, such as a glyoxysome) an endoplasmic reticulum, an endosome, a vacuole, a plasma membrane, a cell wall, a mitochondria, a chloroplast or a plastid.

A chloroplast targeting sequence is any peptide sequence that can target a protein to the chloroplasts or plastids, such as the transit peptide of the small subunit of the alfalfa ribulose-biphosphate carboxylase (Khoudi, et al., Gene, 197:343-351 (1997)).

A peroxisomal targeting sequence refers to any peptide sequence, either N-terminal, internal, or C-terminal, that can target a protein to the peroxisomes, such as the plant C-terminal targeting tripeptide SKL (Banjoko & Trelease, Plant Physiol., 107:1201-1208 (1995); Wallace, et al., "Plant Organellular Targeting Sequences," in Plant Molecular Biology, Ed. R. Croy, BIOS Scientific Publishers Limited (1993) pp. 287-288, and peroxisomal targeting in plant is shown in, Volokita, The Plant J., 361-366 (1991)).

Plastid targeting sequences are known in the art and include the chloroplast small subunit of ribulose-1,5-bisphosphate carboxylase (Rubisco) (de Castro Silva Filho et al. Plant Mol. Biol. 30:769-780 (1996); Schnell et al. J. Biol. Chem. 266(5):3335-3342 (1991)); 5-(enolpyruvyl)shikimate-3-phosphate synthase (EPSPS) (Archer, et al., J. Bioenerg. Biomemb., 22(6):789-810 (1990)); ttryptophan synthase (Zhao et al, J. Biol. Chem., 270(11):6081-6087 (1995)); plastocyanin (Lawrence, et al., J. Biol. Chem., 272(33):20357-20363 (1997)); chorismate synthase (Schmidt, et al., J. Biol. Chem., 268(36):27447-27457 (1993)); and the light harvesting chlorophyll a/b binding protein (LHBP) (Lamppa, et al., J. Biol. Chem., 263:14996-14999 (1988)). See also Von Heijne, et al., Plant Mol. Biol. Rep., 9:104-126 (1991); Clark, et al., J. Biol. Chem. 264: 17544-17550 (1989); Della-Cioppa et al. Plant Physiol. 84:965-968 (1987); Romer et al. Biochem. Biophys. Res. Commun. 196:1414-1421 (1993); and Shah et al. Science, 233:478-481 (1986). Alternative plastid targeting signals have also been described in the following: US 2008/0263728; Miras, et al. J Biol Chem, 277(49) (2002): 47770-8 (2002); Miras, et al., J Biol Chem, 282: 29482-29492 (2007).

F. Selectable Markers

The expression cassettes described herein may encode a selectable marker to enable selection of transformation events. There are many methods that have been described for the selection of transformed plants [for review see (Miki, et al., Journal of Biotechnology, 107:193-232 (2004)) and references cited within]. Selectable marker genes that have been used extensively in plants include the neomycin phosphotransferase gene nptII (U.S. Pat. Nos. 5,034,322, 5,530, 196), hygromycin resistance gene (U.S. Pat. No. 5,668,298), the bar gene encoding resistance to phosphinothricin (U.S. Pat. No. 5,276,268), the expression of aminoglycoside 3"-adenyltransferase (aadA) to confer spectinomycin resistance (U.S. Pat. No. 5,073,675), the use of inhibition resistant 5-enolpyruvyl-3-phosphoshikimate synthetase (U.S. Pat. No. 4,535,060) and methods for producing glyphosate tolerant plants (U.S. Pat. Nos. 5,463,175; 7,045,684). Methods of plant selection that do not use antibiotics or herbicides as a selective agent have been previously described and include expression of glucosamine-6-phosphate deaminase to inactive glucosamine in plant selection medium (U.S. Pat. No. 6,444,878), and a positive/negative system that utilizes D-amino acids (Erikson, et al., Nat Biotechnol, 22:455-8 (2004)). European Patent Publication No. EP 0 530 129 describes a positive selection system which enables the transformed plants to outgrow the non-transformed lines by expressing a transgene encoding an enzyme that activates an inactive compound added to the growth media.

U.S. Pat. No. 5,767,378 describes the use of mannose or xylose for the positive selection of transgenic plants. Methods for positive selection using sorbitol dehydrogenase to convert sorbitol to fructose for plant growth have also been described (WO 2010/102293). Screenable marker genes include the beta-glucuronidase gene (Jefferson, et al., EMBO J., 6:3901-3907 (1987); U.S. Pat. No. 5,268,463) and native or modified green fluorescent protein gene (Cubitt, et al., Trends Biochenz. Sci. 20: 448-455 (1995); Pan, et al., Plant Physiol., 112: 893-900 (1996).

Transformation events can also be selected through visualization of fluorescent proteins such as the fluorescent proteins from the nonbioluminescent Anthozoa species which include DsRed, a red fluorescent protein from the Discosonza genus of coral (Matz, et al., Nat Biotechnol, 17:969-73 (1999)). An improved version of the DsRed protein has been developed (Bevis and Glick, Nat Biotech, 20:83-87 (2002)) for reducing aggregation of the protein. Visual selection can also be performed with the yellow fluorescent proteins (YFP) including the variant with accelerated maturation of the signal (Nagai, et al., Nat Biotech., 20:87-90 (2002)), the blue fluorescent protein, the cyan fluorescent protein, and the green fluorescent protein (Sheen, et al., Plant J, 8:777-84 (1995); Davis and Vierstra, Plant Molecular Biology, 36:521-528 (1998)). A summary of fluorescent proteins can be found in Tzfira, et al., Plant Molecular Biology, 57:503-516 (2005) and Verkhusha and Lukyanov Nat Biotech, 22:289-296 (2004)). Improved versions of many of the fluorescent proteins have been made for various applications. Use of the improved versions of these proteins or the use of combinations of these proteins for selection of transformants will be obvious to those skilled in the art. It is also practical to simply analyze progeny from transformation events for the presence of the PHB thereby avoiding the use of any selectable marker.

For plastid transformation constructs, a preferred selectable marker is the spectinomycin-resistant allele of the plastid 16S ribosomal RNA gene (Staub and Maliga, Plant Cell, 4:39-45 (1992); Svab, et al., Proc. Natl. Acad. Sci. USA, 87: 8526-8530 (1990)). Selectable markers that have since been successfully used in plastid transformation include the bacterial aadA gene that encodes aminoglycoside 3'-adenyltransferase (AadA) conferring spectinomycin and streptomycin resistance (Svab, et al., Proc. Natl. Acad. Sci. USA, 90:913-917 (1993)), nptH that encodes aminoglycoside phosphotransferase for selection on kanamycin (Carrer, et al., MoL Gen. Genet., 241:49-56 (1993); Lutz, et al., Plant J., 37: 906-913 (2004); Lutz, et al., Plant Physiol., 145: 1201-1210 (2007)), aphA6, another aminoglycoside phosphotransferase (Huang, et al, Mol. Genet. Genomics, 268: 19-27 (2002)), and chloramphenicol acetyltransferase (Li, et al. Plant Mol Biol, 76(5-6):443-451 (2010)). Another selection scheme has been reported that uses a chimeric betaine aldehyde dehydrogenase gene (BADH) capable of converting toxic betaine aldehyde to nontoxic glycine betaine (Daniell, et al., *Curr. Genet.*, 39: 109-116 (2001)).

Transgenic Plants/Plant Material

A wide variety of plants and plant cell systems can be engineered to express an OsACBP5 polypeptide or a functional fragment or variant of OsACBP5. Plant material such as leaves, stems, roots, flowers or flower parts, fruits, pollen, egg cells, zygotes, seeds, cuttings, cell or tissue cultures, or any other part or product of a plant can thus be obtained, thus genetically modified show improved tolerance to fungal necrotrophs.

The genetically modified plant or plant material comprises one or more genes encoding an OsACBP5 polypeptide or a functional fragment or variant of OsACBP5. In some embodiments the genetically modified plant/plant material comprises two nucleotide sequences encoding the two or more OsACBP5s, which may each be contained on separate expression vectors, or, on single expression vector under the control of a common promoter.

In preferred embodiments, target plants and plant cells for engineering include monocotyledonous and dicotyledonous plants, such as crops, including grain crops (for example, wheat, maize, rice, millet, barley), tobacco, fruit crops (for example, tomato, strawberry, orange, grapefruit, banana), forage crops (for example, alfalfa), root vegetable crops (for example, carrot, potato, sugar beets, yam), leafy vegetable crops (for example, lettuce, spinach); flowering plants (for example, petunia, rose, chrysanthemum), conifers and pine trees (for example, pine fir, spruce); oil crops (for example, sunflower, rape seed); and plants used for experimental purposes (for example, *Arabidopsis*). Other examples include plants that are typically grown in groups of more than about 10 plants in order to harvest the entire plant or a part of the plant, for example, a fruit, a flower or a crop, for example, tobacco, grain, that the plants bear, etc.), trees (i.e., fruit trees, trees grown for wood production, trees grown for decoration, etc.), flowers of any kind (i.e., plants grown for purposes of decoration, for example, following their harvest), cactuses. Further examples of plants in which the OsACBP5s may be expressed include *Viridiplantae, Streptophyta, Embryophyta, Tracheophyta, Euphyllophytes, Spermatophyta, Magnoliophyta, Liliopsida, Commelinidae, Poales, Poaceae, Oryza, Oryza sativa, Zea, Zea mays, Hordeum, Hordeum vulgare, Triticum, Triticum aestivum, Eudicotyledons, Core eudicots, Asteridae, Euasterids, Rosidae, Eurosids II, Brassicales, Brassicaceae, Arabidopsis, Magnoliopsida, Solananae, Solanales, Solanaceae, Solanum,* and *Nicotiana.*

Additional plants that can be transformed using the vectors described herein include, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Panneserum, Persea, Phaseolus, Pistachia, Pisum, Pyrus, Prunus, Raphanus, Ricinus, Secale, Senecio, Sinapis, Solanum, Sorghum, Theobromus, Trigonella, Talcum, Vicia, Vitis, Vigna,* and *Zea.*

Method for Producing Fungal Resistant Plant/Plant Cells

The plants and plant cells/material described herein may be obtained by engineering one or more of the vectors expressing an OsACBP5 polypeptide or a functional fragment or variant of OsACBP5 as described herein into a variety of plant cell types, including but not limited to, protoplasts, tissue culture cells, tissue and organ explants, pollens, embryos, as well as whole plants.

Transformation protocols as well as protocols for introducing nucleotide sequences into plants may vary depending on the type of plant or plant cell targeted for transformation. Suitable methods of introducing nucleotide sequences into plant cells and subsequent insertion into the plant genome include microinjection (Crossway, et al., *Biotechniques,* 4:320-334 (1986)), electroporation (Riggs, et al., *Proc. Natl. Acad. Sci. USA,* 83:5602-5606 (1986)), Agrobacterium-mediated transformation (Townsend, et al., U.S. Pat. No. 5,563,055; Horsch, et al., *Science,* 227: 1227-1231 (1985)), direct gene transfer (Paszkowski, et al. *EMBO J.,* 3:2717-2722 (1984)), and ballistic particle acceleration (see, for example, Sanford et al., U.S. Pat. No. 4,945,050; Tomes, et al., Plant Cell, Tissue, and Organ Culture: Fundamental Methods, ed. Gamborg and Phillips (Springer-Verlag, Berlin) (1995); and McCabe, et al., *Biotechnology* 6:923-926 (1988)). Also see Weissinger, et al. *Ann. Rev. Genet.,* 22:421-477 (1988); Sanford, et al., *Particulate Science and Technology,* 5:27-(1987) (onion); Christou, et al., *Plant Physiol.,* 87:671-674 (1988) (soybean); McCabe, et al., *BioTechnology,* 6:923-926 (1988) (soybean); Finer and McMullen, *In Vitro Cell Dev. Biol.,* 27P:175-182 (1991) (soybean); Singh, et al., *Theor. Appl. Genet.,* 96:319-324 (1998)(soybean); Dafta, et al., *Biotechnology,* 8:736-740 (1990) (rice); Klein, et al., *Proc. Natl. Acad. Sci. USA,* 85:4305-(1988) (maize); Klein, et al., *Biotechnology,* 6:559-563 (1988) (maize); Tomes, U.S. Pat. No. 5,240,855; Buising, et al., U.S. Pat. Nos. 5,322,783 and 5,324,646; Tomes, et al. (1995) in Plant Cell, Tissue, and Organ Culture: Fundamental Methods, ed. Gamborg (Springer-Verlag, Berlin) (maize); Klein, et al., *Plant Physiol.,* 91:440-444 (1988) (maize); Fromm, et al., *Biotechnology,* 8:833-839 (1990) (maize); Hooykaas-Van Slogteren, et al., *Nature,* 311:763-764 (1984); Bowen, et al., U.S. Pat. No. 5,736,369 (cereals); Bytebier, et al., *Proc. Natl. Acad. Sci. USA,* 84:5345-5349 (1987) (Liliaceae); De Wet, et al. in The Experimental Manipulation of Ovule Tissues, ed. Chapman et al. (Longman, N.Y.), pp. 197-209 (1985) (pollen); Kaeppler et al. *Plant Cell Reports* 9:415-418 (1990) and Kaeppler, et al., *Theor. Appl. Genet.,* 84:560-566 (1992) (whisker-mediated transformation); D'Halluin, et al., *Plant Cell* 4:1495-1505 (1992) (electroporation); Li, et al., *Plant Cell Reports,* 12:250-255 (1993); Christou and Ford, *Annals of Botany,* 75:407-413 (1995) (rice); Osjoda, et al., *Nature Biotechnology,* 14:745-750 (1996) (maize via *Agrobacterium tumefaciens*).

Methods for protoplast transformation and/or gene gun for Agrisoma technology are described in WO 2010/037209. Methods for transforming plant protoplasts are available including transformation using polyethylene glycol (PEG), electroporation, and calcium phosphate precipitation (see for example Potrykus, et al., *Mal. Gen. Genet.,* 199:183-188 (1985); Potrykus, et al., *Plant Molecular Biology Reporter,* 3:117-128 (1985). Methods for plant regeneration from protoplasts have also been described [Evans et al., in Handbook of Plant Cell Culture, Vol 1, (Macmillan Publishing Co., New York, 1983); Vasil, I K in Cell Culture and Somatic Cell Genetics (Academic, Orlando, 1984)].

Methods for transformation of plastids such as chloroplasts are known in the art. See, for example, Svab, et al., *Proc. Natl. Acad. Sci. USA,* 87:8526-(1990); Svab and Maliga, *Proc. Natl. Acad. Sci. USA,* 90:913-917 (1993); Svab and Maliga, *EMBO J.* 12:601-606 (1993) and Staub and Maliga, *Plant J.* 6:547-553 (1994); Kuehnle, US Publication No. 2009/7618819. The method relies on particle gun delivery of DNA containing a selectable marker and targeting of the DNA to the plastid genome through homologous recombination. Additionally, plastid transformation may be accomplished by transactivation of a silent plastid-borne transgene by tissue-preferred expression of a nuclear-encoded and plastid-directed RNA polymerase (McBride, et al., *Proc. Natl. Acad. Sci. USA*, 91:7301-7305 (1994)) or by use of an integrase, such as the phiC31 phage site-specific integrase, to target the gene insertion to a previously inserted phage attachment site (Lutz, et al., *Plant J.* 37:906-13 (2004)). Plastid transformation vectors can be designed such that the transgenes are expressed from a promoter sequence that has been inserted with the transgene during the plastid transformation process or, alternatively, from an endogenous plastidial promoter such that an extension of an existing plastidial operon is achieved (Herz, et al., *Transgenic Research*, 14:969-982 (2005)). An alternative method for plastid transformation as described in WO 2010/061186 wherein RNA produced in the nucleus of a plant cell can be targeted to the plastid genome can also be used. Inducible gene expression from the plastid genome using a synthetic riboswitch has also been reported (Verhounig, et al., *Proc Natl Acad Sci USA*, 107: 6204-6209 (2010)). Methods for designing plastid transformation vectors are described by Lutz, et al., *Plant Physiol*, 145:1201-10 (2007).

Recombinase technologies which are useful for producing the disclosed transgenic plants include the cre-lox, FLP/FRT and Gin systems. Methods by which these technologies can be used for the purpose described herein are described for example in U.S. Pat. No. 5,527,695; Dale And Ow, *Proc. Natl. Acad. Sci. USA*, 88:10558-10562 (1991); Medberry, et al., *Nucleic Acids Res.* 23:485-490 (1995).

The engineered plant/plant material is selected or screened for transformants (i.e., those that have incorporated or integrated the introduced gene construct(s)) following the approaches and methods described below or screening methods known in the art. Following transformation by any one of the methods described above, procedures that can be used to obtain a transformed plant expressing the transgenes include, but are not limited to: selecting the plant cells that have been transformed on a selective medium; regenerating the plant cells that have been transformed to produce differentiated plants; selecting transformed plants expressing the transgene producing the desired level of desired polypeptide(s) in the desired tissue and cellular location.

A transformed plant cell, callus, tissue, or plant may be identified and isolated by selecting or screening the engineered plant material for traits encoded by the selection marker genes present on the introduced expression cassette. For instance, selection may be performed by growing the engineered plant material on media containing inhibitory amount of the antibiotic or herbicide to which the transforming gene construct confers resistance. Particularly, the selectable marker gene nptII, which specifies kanamycin-resistance, can be used in nuclear transformation. Further, transformed plants and plant material may also be identified by screening for the activities of any visible marker genes (e.g., the β-glucuronidase, luciferase, B or C1 genes) that may be present on the vectors described herein. Such selection and screening methodologies are well known to those skilled in the art. Alternatively or in addition, screening may be for improved tolerance to fungal necrotrophs as taught herein, for example, by observing a reduction in growth-inhibition.

Physical and biochemical methods may also be used to identify plant or plant cell transformants containing the gene constructs/vectors described herein. These methods include, but are not limited to: 1) Southern analysis or PCR amplification for detecting and determining the structure of the recombinant DNA insert; 2) Northern blot, 51 RNase protection, primer-extension or reverse transcriptase-PCR amplification for detecting and examining RNA transcripts of the gene constructs; 3) enzymatic assays for detecting enzyme activity, where such gene products are encoded by the gene construct; 4) protein gel electrophoresis (PAGE), western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

The cells that have been transformed may be grown into plants in accordance with conventional techniques. See, for example, McCormick, et al., *Plant Cell Reports* 5:81-84 (1986). These plants may be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved. An isolated transformant may be regenerated into a plant and progeny thereof (including the immediate and subsequent generations) via sexual or asexual reproduction or growth. Alternatively, the engineered plant material may be regenerated into a plant before subjecting the derived plant to selection or screening for the marker gene traits. Procedures for regenerating plants from plant cells, tissues or organs, either before or after selecting or screening for marker gene(s), are well known to those skilled in the art.

In plastid transformation procedures, further rounds of regeneration of plants from explants of a transformed plant or tissue can be performed to increase the number of transgenic plastids such that the transformed plant reaches a state of homoplasmy (all plastids contain uniform plastomes containing transgene insert).

Method for Identifying Genes which Confer Fungal Resistance

Methods are provided for identifying variants and homologs of OsACBP5 that confer fungal resistance. An exemplary screening method involves introducing an exogenous nucleic acid into a host cell, producing a test cell, where the host cell is one that exhibits growth inhibition in fungal conditions when water is restricted or withheld to a growth-inhibiting level for a growth-inhibiting period of time. When an exogenous nucleic acid comprising a nucleotide sequence that encodes an OsACBP5 or OsACBP5-like polypeptide is introduced into the host cell, growth inhibition of the test cell is enhanced. Thus, a reduction in growth inhibition indicates that the exogenous nucleic acid encodes an OsACBP5 or OsACBP5-like polypeptide, where the encoded polypeptide is produced at a level and/or has an activity that relieves the fungal-induced growth inhibition. A reduction in growth inhibition includes an at least about 10%, at least about 20%, at least about 30%, at least about 40%, at least about 50%, at least about 60%, at least about 70%, at least about 80%, at least about 90%, or more, reduction in growth inhibition as compared to a non-genetically-modified host.

To generate a subject genetically modified host cell, one or more nucleic acids including nucleotide sequences encoding one or more OsACBP5 polypeptides that convey tolerance to fungal necrotrophs is introduced stably or transiently into a parent host cell, using established techniques, including, but not limited to, electroporation, calcium phosphate precipitation, DEAE-dextran mediated transfection, liposome-mediated transfection, particle bombardment, *Agrobacterium*-mediated transformation, and the like. For stable transformation, a nucleic acid will generally further include a selectable marker, for example, any of several well-known selectable markers such as neomycin resistance, ampicillin resistance, tetracycline resistance, chloramphenicol resistance, and kanamycin resistance.

The exogenous nucleic acid is inserted into an expression vector. Expression vectors that are suitable for use in prokaryotic and eukaryotic host cells are known in the art, and any suitable expression vector can be used. Examples among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used.

The appropriate nucleotide sequence may be inserted into an expression system by any of a variety of well-known and routine techniques, such as, for example, those set forth in Sambrook et al., Molecular Cloning, A Laboratory Manual (2nd Ed., Cold Spring Harbor Laboratory Press, Cold Spring Harbor, N.Y. (1989)). Where a parent host cell has been genetically modified to produce two or more OsACBP5s, nucleotide sequences encoding the two or more OsACBP5s will in some embodiments each be contained on separate expression vectors; or in some embodiments, are contained on a single expression vector, operably linked to a common control element (for example, a promoter).

An exogenous nucleic acid will in some embodiments be isolated from a cell or an organism in its natural environment. Methods of isolating the exogenous nucleic acid from test cell are well known in the art. Suitable methods include, but are not limited to, any of a number of alkaline lysis methods that are standard in the art. In other embodiments, the nucleic acid of the cell or organism will be mutated before nucleic acid is isolated from the cell or organism. In other embodiments, the exogenous nucleic acid is synthesized in a cell-free system in vitro.

In some embodiments, the screening method includes further characterizing a candidate gene product. In these embodiments, the exogenous nucleic acid comprising nucleotide sequence(s) encoding an OsACBP5(s) are isolated from a test cell as described above. The isolated nucleic acid may be subjected to nucleotide sequence analysis, and the amino acid sequence of the gene product deduced from the nucleotide sequence. In some embodiments, the amino acid sequence of the gene product is compared with other amino acid sequences in a public database of amino acid sequences, to determine whether any significant amino acid sequence identity to an amino acid sequence of a known protein exists.

After the exogenous gene has been identified as having the ability to confer fungal resistance, this newly identified OsACBP5 variant/homolog can be used to provide plants/plant cells with improved fungal resistance.

A. Exogenous Nucleic Acids

Exogenous nucleic acids that are suitable for introducing into a host cell, to produce a test cell, include, but are not limited to, naturally-occurring nucleic acids isolated from a cell. Exogenous nucleic acids to be introduced into a host cell may be identified by hybridization under stringent conditions to a nucleic acid encoding OsACBP5. Exogenous sequences which show 77% or more nucleotide sequence homology with OsACBP5 can also be introduced into a host cell to form a test cell. An OsACBP5-like sequence is with at least 77% DNA homology to OsACBP5 and is capable of upregulating cell wall proteins (FLA10, LRX4, LRX5, XTH4, PME18), proteins involved in secondary metabolism (ESM1, Myrosinase1, Myrosinase2, NIT1) and jasmonic acid synthesis protein (AOC2) upon pathogen infection. More preferably, the sequence homology is, 80% or greater, most preferably, 90% or greater.

Naturally-occurring nucleic acids that have been modified (for example, by mutation) before or subsequent to isolation from a cell; synthetic nucleic acids, e.g., nucleic acids synthesized in a laboratory using standard methods of chemical synthesis of nucleic acids, or generated by recombinant methods; synthetic or naturally-occurring nucleic acids that have been amplified in vitro, either within a cell or in a cell-free system; and the like. Exemplary exogenous nucleic acids include, but are not limited to, genomic DNA; RNA; a complementary DNA (cDNA) copy of mRNA isolated from a cell; recombinant DNA; and DNA synthesized in vitro, e.g., using standard cell-free in vitro methods for DNA synthesis. In some embodiments, exogenous nucleic acids are a cDNA library made from cells, either prokaryotic cells or eukaryotic cells.

In some embodiments, for example, where the exogenous nucleic acid is a plurality of exogenous nucleic acids (such as, for example, a cDNA library, a genomic library, or a population of nucleic acids, each encoding an OsACBP5 or OsACBP5-like polypeptide with a different amino acid sequence, etc.), the exogenous nucleic acids are introduced into a plurality of host cells, forming a plurality of test cells. The test cells are in some embodiments grown in culture under fungal conditions such that native cells of the same type would exhibit growth inhibition and/or death; those test cells comprising an exogenous nucleic acid that comprises nucleotide sequences encoding an OsACBP5/OsACBP5-like polypeptide will grow faster than test cells that do not comprise an exogenous nucleic acid that comprises nucleotide sequences encoding an OsACBP5/OsACBP5-like polypeptide, or those test cells comprising an exogenous nucleic acid that comprises nucleotide sequences encoding an OsACBP5/OsACBP5-like polypeptide will live, while test cells that do not comprise an exogenous nucleic acid that comprises nucleotide sequences encoding OsACBP5/OsACBP5-like polypeptide will die or otherwise be adversely affected.

In other embodiments, the exogenous nucleic acid is a synthetic nucleic acid which comprises for example, a nucleotide sequence encoding a variant OsACBP5, for example, an OsACBP5 that differs in amino acid sequence by one or more amino acids from a naturally-occurring OsACBP5 or other parent OsACBP5. In some embodiments, a variant OsACBP5 differs in amino acid sequence by one amino acid, two amino acids, three amino acids, four amino acids, five amino acids, six amino acids, seven amino acids, eight amino acids, nine amino acids, or ten amino acids, or more, compared to the amino acid sequence of a naturally-occurring parent OsACBP5. In some embodiments, a variant OsACBP5 differs in amino acid sequence by from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 50 amino acids, or from about 50 amino acids to about 60 amino acids, compared to the amino acid sequence of a naturally-occurring parent OsACBP5.

Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available. Fragments of full-length proteins can be produced by techniques well known in the art, such as by creating synthetic nucleic acids encoding the desired portions; or by use of Bal 31 exonuclease to generate fragments of a longer nucleic acid.

In still other embodiments, a variant OsACBP5 is encoded by a nucleic acid that hybridizes under stringent conditions to a nucleic acid encoding an *Oryza sativa* ACBP5 or another known OsACBP5.

Nucleic acids will in some embodiments be mutated before being introduced into a host cell to form the test cell. In these embodiments, a nucleic acid comprising a nucleotide sequence encoding a naturally-occurring OsACBP5 is mutated, using any of a variety of well-established methods, giving rise to a nucleic acid comprising a nucleotide sequence encoding a variant OsACBP5. Nucleotide sequences encoding OsACBP5s are known in the art, and any known OsACBP5-encoding nucleotide sequence can be altered to generate a synthetic nucleic acid for use in a subject method.

Methods of mutating a nucleic acid are well known in the art and include well-established chemical mutation methods, radiation-induced mutagenesis, and methods of mutating a nucleic acid during synthesis. Chemical methods of mutating DNA include exposure of DNA to a chemical mutagen, e.g., ethyl methanesulfonate (EMS), methyl methanesulfonate (MMS), N-nitrosourea (ENU), N-methyl-N-nitro-N'-nitrosoguanidine, 4-nitroquinoline N-oxide, diethylsulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, gamma-irradiation, X-rays, and fast neutron bombardment. Mutations can also be introduced into a nucleic acid using, e.g., trimethylpsoralen with ultraviolet light. Random or targeted insertion of a mobile DNA element, e.g., a transposable element, is another suitable method for generating mutations. Mutations can be introduced into a nucleic acid during amplification in a cell-free in vitro system, e.g., using a polymerase chain reaction (PCR) technique such as error-prone PCR. Mutations can be introduced into a nucleic acid in vitro using DNA shuffling techniques (e.g., exon shuffling, domain swapping, and the like). Mutations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Methods of mutating nucleic acids are well known in the art, and any known method is suitable for use. See, e.g., Stemple, *Nature Reviews*, 5:1-7 (2004); Chiang et al., *PCR Methods Appl.*, 2:210-217 (2003); Stemmer, *Proc. Natl. Acad. Sci. USA*, 91:10747-10751 (1994); and U.S. Pat. Nos. 6,033,861, and 6,773,900.

Thus, for example, a nucleic acid comprising a nucleotide sequence encoding a naturally-occurring OsACBP5 is exposed to a chemical mutagen, as described above, or subjected to radiation mutation, or subjected to an error-prone PCR, and the mutagenized nucleic acid introduced into a genetically modified host cell(s) as described above. Methods for random mutagenesis using a "mutator" strain of bacteria are also well known in the art and can be used to generate a variant OsACBP5. See, e.g., Greener, et al., *Methods in Molecular Biology*, 57:375-385 (1995). Saturation mutagenesis techniques employing a polymerase chain reaction (PCR) are also well known and can be used. See e.g., U.S. Pat. No. 6,171,820. Nucleic acids comprising a nucleotide sequence encoding a variant OsACBP5 are identified by the ability to relieve growth inhibitions caused by lead.

B. Host Cells

The host cell useful in the screening methods described herein can be a eukaryotic cell, a prokaryotic cell, or a cell from a multicellular organism (for example, a cell line).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); and the like.

Example 1. OsACBP5 is Induced by Necrotrophic Fungal Pathogen *Rhizoctonia solani* Infection The present invention showed that of the six OsACBPs, only OsACBP5 was induced upon necrotrophic fungal pathogen *Rhizoctonia solani* challenge in quantitative real-time PCR analysis upon infection of wild-type rice with the fungal necrotrophic pathogen *R. solani* (FIG. 1). The necrotrophic fungal pathogen *R. solani* was cultured on potato dextrose agar (PDA) at 23° C. for 7 days (Keijer et al., *Plant Pathology*, 46:659-669 (1997)). In detail, total RNA (5 µg) of 2-week-old wild-type seedlings infected with the fungal necrotrophic pathogen *R. solani* were extracted using RNeasy Plant Mini Kit (Qiagen; catalog no. 74904) and were reverse transcribed into the first strand cDNA using the SuperScript First-Strand Synthesis System (Invitrogen; catalog no. 12371-019). Quantitative RT-PCR (qRT-PCR) was carried out with a StepOne Plus real-time PCR system (Applied Biosystems, Foster City, Calif., USA) and Fast-Start Universal SYBR Green Mater (Roche). The conditions for qRT-PCR were as follows: denaturation at 95° C. for 10 min, followed by 40 cycles of 95° C. for 15 s and 60° C. for 1 min. Three experimental replicates for each reaction were carried out using specific primers to the gene of interest and a rice actin as internal control. The relative changes of gene expression levels were analysed according to Schmittgen and Livak (Schmittgen and Livak, *Nat. Protoc.* 3:1101-1108, (2008)) from three independent experiments. Provided below are primers used for qRT-PCR analysis:

| Gene name | Primer name | Sequence | Product size (bp) |
|---|---|---|---|
| Actin | ML1115 SEQ ID NO: 1 | 5'-AGGCCGTCCTCTCTCTGTAT-3' | 107 |
|  | ML1116 SEQ ID NO: 2 | 5'-GGGGAGAGCATATCCTTCAT-3' |  |
| OsACBP1 | ML1103 SEQ ID NO: 3 | 5'-TGTCAATACTGCTCGTCCTG-3' | 105 |
|  | ML1104 SEQ ID NO: 4 | 5'-TAGTCGCTCATTGCTTCCTC-3' |  |
| OsACBP2 | ML1105 SEQ ID NO: 5 | 5'-ATGGGTTTGCAGGAGGAGTTT-3' | 105 |
|  | ML1106 SEQ ID NO: 6 | 5'-CTGCTTGTAGAGGCCATAGAG-3' |  |
| OsACBP3 | ML1107 SEQ ID NO: 7 | 5'-TGGGTCTGCAGGAGGATTTTG-3' | 112 |
|  | ML1108 SEQ ID NO: 8 | 5'-ACGGTGGCCTGCTTGTAGAGT-3' |  |
| OsACBP4 | ML1109 SEQ ID NO: 9 | 5'-GCATCTGGCTGCTGGTGTAG-3' | 117 |
|  | ML1110 SEQ ID NO: 10 | 5'-GCATTTGCATTGACAAGAATCT-3' |  |
| OsACBP5 | ML1111 SEQ ID NO: 11 | 5'-GAGGCTATTCCAGGATGGAT-3' | 119 |
|  | ML1112 SEQ ID NO: 12 | 5'-CTGTCATGTTGGTTGATTGTAT-3' |  |
| OsACBP6 | ML1113 SEQ ID NO: 13 | 5'-GGTGGTGGCAATAACAAAAG-3' | 104 |
|  | ML1114 SEQ ID NO: 14 | 5'-GCAAGGGGAACACGACCTT-3' |  |

The OsACBP5 full-length cDNA (SEQ ID NO:15) is provided below (highlighted in red are the OsACBP5 specific primers used for qRT-PCR):

ggttgctcgatcgtctcgctctcctctcctcttctcttcgtctctcctcctgaccttttccgctttccttttccccctcctcgatccgc Start codon ggcgcaaccgaacacgaaagcgagagagagaggagtgcagccgctgccctgtccctcaccgcgccgcgccgacatggag ctgttctacgagctgctcctcacggcggctgcctccctcctcgtcgccttcctgctggccaggctgctggcctccgccgccaccg -continued
```
ccagtgatccccgccgccgcgcgcccgatcacgccgccgtgatcgcggaggaggaggcggtggtggtggaggaggagag gatcatcgaggtcgatgaggtcgaggtgaagagcgcgcgcgcgagggagtgcgtggtttcggaggggtgggtcgaggtggg gagggcctcgtcggcggaggggaagctcgagtgcttgccggaggaagaggaggctcccgcgaaggccgctcgggagcttg ttctcgatgccgttttggaggaacgcgaggaggaaggacaagttggcgaagagcggtgcgatttggccgctgcggtggcgga ggtcgtgggagtgaagccgcatgagttgggggttgaagctgctcccggggaggtatctgacgtgacgctggaggaagggaa ggtgcaggatgttggggtggagcagcatgatttggtcgccgaggctgctccaagggaagctcttgacacaggggttggagaaac agggtgttcccatcattgaagcggttgaaatcaagcggcaggatgatctgggtgctgaggtagctccgagtgacgttcctgaggt ggaatttgagcaacagggagttcgcattattgaagctattgatgtgaatcaacatcatcgggttgctctggctgctcctgcggaagt tgttgatgcgggattggaggagagggtccaagctattgaagcagggtcatctggattgacttccgagacagttcctgaagaggtt cttgacgagttatctgagaagcaagaagagcaagttattgaagagaaggaacatcaattggctgcagcgactgctccagtagca attcctggtgtggcattggcagagacggaggaacttaaagaagaacaatcctctgaaaaagctgtcaatgttcatgaagaagttc agagtaaggacgaagctaaatgcaagctccatctggttgatcaacaagaaggttcggcttctaaggtggagctggtggggagg aataccgacaatgtggaaattagccatggaagcagttctggtgacaaaatgattgctgagttgaccgaggaggaattgacattgc aaggtgtgcccgcagatgagactcagacagacatggaatttggggagtgggaagggattgaaagaactgagatagaaaagag gtttggtgtggcagcagcgtttgcatctagtgacgccgggatggctgccctgtcaaagcttgatagtgatgtgcagctgcagctg cagggactccttaaggttgccattgatggtccatgctatgactctacacagccacttaccttgaggccttcatctcgtgcaaaatgg
```
                                                                 ML1111
```
gctgcttggcaaaagctagggaacatgtatccggagacagctatggaaagatacatgaatctttgtcagaggctattccaggat ggatgggtgacaatatctcgggcacaaaggaacatgaagctggtgatgatgctgtagggtctgtcttaacaatgacttcaaatac
```
ML1112
```
aatcaaccaacatgacagtcaagggaatgaagacaatactggcatgtatgaaggtcacttgacaagttcccctaacccagaaa aggacagagttctgacatccctgctgaggtgaatgaacataacactcatggaagatttcttgcatcagtgatttcagcccattgctg
```
                    Stop codon
```
agaccgctaccgatgccttcctcataagattagatttgtacagtgctcctgtggtgctaatattagtgttgtcatggtgttggtttgtgt atatatgactgtatatatcagtaactgccggtcctactgcgtgtattccgccagcagcagacttatcatctggtattctggtgtagt ctgtagaacaatacatctggtgagtcgtaattatatgtcgatacgatgcagtttggaaggagaaattgaagtggttggaaaaccagt tgaaaggac
```

The amino acid sequence of OsACBP5 (SEQ ID NO:16) is provided below.

3'
MELFYELLLTAAASLLVAFLLARLLASAATASDPRRRAPDHAAVIAEEEA

VVVEEERIIEVDEVEVKSARARECVVSEGWVEVGRASSAEGKLECLPEEE

3'
EAPAKAARELVLDAVLEEREEEGQVGEERCDLAAAVAEVVGVKPHELGVE

AAPGEVSDVTLEEGKVQDVGVEQHDLVAEAAPREALDTGLEKQGVPIIEA

VEIKRQDDLGAEVAPSDVPEVEFEQQGVRIIEAIDVNQHHRVALAAPAEV

VDAGLEERVQAIEAGSSGLTSETVPEEVLDELSEKQEEQVIEEKEHQLAA

ATAPVAIPGVALAETEELKEEQSSEKAVNVHEEVQSKDEAKCKLHLVDQQ

EGSASKVELVGRNTDNVEISHGSSSGDKMIAELTEEELTLQGVPADETQT

DMEFGEWEGIERTEIEKRFGVAAAFASSDAGMAALSKLDSDVQLQLQGLL

KVAIDGPCYDSTQPLTLRPSSRAKWAAWQKLGNMYPETAMERYMNLLSEM

PGWMGDNISGTKEHEAGDDAVGSVLTMTSNTINQHDSQGNEDNTGMYEGH

LTSSPNPEKGQSSDEPAE

Example 2. Pathogen Assays of Transgenic *Arabidopsis* Lines Over-Expressing 35S::OsACBP5::GFP Against Fungal Necrotrophs *Botrytis Cinerea, Alternaria Brassicicola* and *Rhizoctonia solani*

*Arabidopsis* plants overexpressing 35S::OsACBP5::GFP generated by Meng et al (*New Phytologist*, 203: 469-482 (2014)) originally for GFP subcellular localization studies, were tested against necrotrophic fungal pathogens including the root-infecting necrotroph *Rhizoctonia solani* and shoot-infecting necrotrophs (*Botrytis cinerea* and *Alternaria brassicicola*). The controls used were wild-type *Arabidopsis* (Col-0) and the vector (pBI-eGFP)-transformed lines.

Example 2.1. Whole Plant and Detached Leaf
Assays on Transgenic *Arabidopsis* Lines Using the
Necrotrophic Fungal Pathogen *Botrytis Cinerea*
Show OsACBP5 Confer Protection The necrotrophic fungal pathogen *Botrytis cinerea* was grown on potato dextrose agar and incubated at 22° C. for 2 weeks (Ferrari et al, *Plant Physiology*, 144:367-379 (2007)). Conidiospores were collected from 2-week-old cultures of the necrotrophic fungus *B. cinerea* in 3 ml of water. A haemocytometer was used to adjust the spore numbers to 500000 spores per ml in 1% glucose solution (Ferrari et al, *Plant Physiology*, 144:367-379 (2007)).

Four-week-old transgenic *Arabidopsis* plants transformed with 35S::AtACBP3::GFP, 35S::OsACBP5::GFP, the vector (pBI-eGFP) control and *Arabidopsis* wild-type in compost were sprayed with 5 ml of conidial suspension using a hand-held dispenser. The inoculated pots were kept at 22° C. with 16-h-light and 8-h-dark photoperiods and were covered with polythene bags to maintain humidity until symptoms appears on the plant (approximately a week) (Xiao and Chye, *Plant Physiology*, 156:2069-2081, (2011)).

Detached leaf assays were performed using a single leaf from six-week-old transgenic *Arabidopsis* plants transformed with 35S::AtACBP3::GFP, 35S::OsACBP5::GFP lines, the vector (pBI-eGFP) control and *Arabidopsis* wild-type. The leaf was placed on 1% water agar plates. One drop (10 µl) of the conidial suspension was placed on the surface of each leaf. The inoculated leaves on agar plates were sealed with plant tissue culture tape to maintain humidity and then incubated at 22° C. with constant light (Ferrari et al, *Plant Physiology*, 144:367-379 (2007)).

Disease assessment for whole plant assays and detached leaf assays were carried out by measuring disease incidence and disease severity, respectively as described by Van de Mortel et al. *Plant Physiology*, pp-112 (2012). The disease incidence was calculated as given below:

$$\text{Disease incidence }\% = \frac{\text{Number of infected (necrotic) leaves} \times 100}{\text{Total number of leaves}}$$

Disease severity was calculated by measuring the diameter of the necrotic lesions formed in the leaves as a result of fungal infection.

Figure 2:
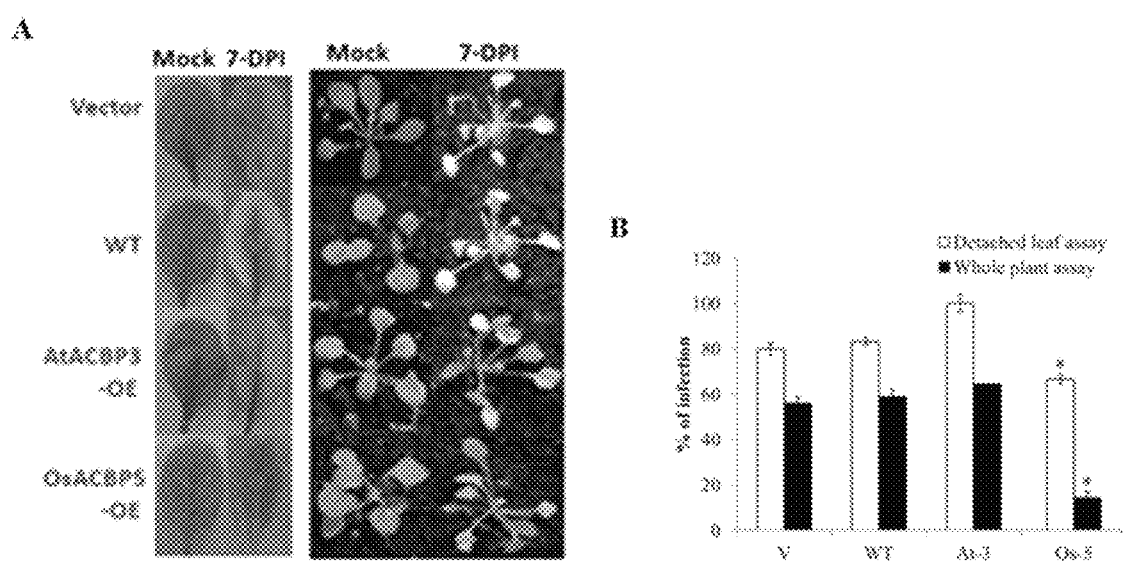

The results (FIG. 2A) revealed that OsACBP5 protected against the necrotrophic fungus *Botrytis cinerea* when it was overexpressed in transgenic *Arabidopsis*. Disease assessment in both assays 7 days post inoculation (DPI), by measuring disease incidence and disease severity following the procedures of Van de Mortel et al. *Plant Physiology*, pp-112 (2012) indicated that infection was statistically lower in the transgenic *Arabidopsis* OsACBP5-OE line, suggesting that OsACBP5 is more effective against the necrotrophic fungus *Botrytis cinerea* (FIG. 2B).

Example 2.2. Whole Plant and Detached Leaf
Assays on Transgenic *Arabidopsis* Lines Using the
Necrotrophic Fungal Pathogen *Alternaria
brassicicola* Show OsACBP5 Confer Protection The necrotrophic fungus *Alternaria brassicicola* was grown on V8 agar medium and incubated at 28° C. for 10 days (Botanga et al., *Molecular Plant-Microbe Interactions*, 25:1628-1638 (2012)). Conidiospores were collected from 2-week-old cultures of the necrotrophic fungus *A. brassicicola* in 3 ml of water. A haemocytometer was used to adjust the spore numbers to 500000 spores per ml in 1% glucose solution (Botanga et al., *Molecular Plant-Microbe Interactions*, 25:1628-1638 (2012)).

Four-week-old transgenic *Arabidopsis* plants transformed with 35S::AtACBP3::GFP, 35S::OsACBP5::GFP, the vector (pBI-eGFP) control and *Arabidopsis* wild-type in compost were sprayed with 5 ml of conidial suspension using a hand-held dispenser. The inoculated pots were kept at 22° C. with 16-h-light and 8-h-dark photoperiods and were covered with polythene bags to maintain humidity. Results were analyzed 7 DPI (Botanga et al., *Molecular Plant-Microbe Interactions*, 25:1628-1638 (2012)).

Detached leaf assays were performed using a single leaf from six-week-old transgenic *Arabidopsis* plants transformed with 35S::AtACBP3::GFP, 35S::OsACBP5::GFP, the vector (pBI-eGFP) control and *Arabidopsis* wild-type. The *Arabidopsis* leaf was placed on 1% water agar plates. One drop (10 µl) of the conidial suspension was placed on the surface of each leaf. The inoculated *Arabidopsis* leaves on agar plates were sealed with plant tissue culture tape to maintain humidity and then incubated at 22° C. with constant light (Botanga et al., *Molecular Plant-Microbe Interactions*, 25:1628-1638 (2012)).

Disease assessment for whole plant assays and detached leaf assays were carried out by measuring disease incidence and disease severity, respectively as suggested by Van de Mortel et al. *Plant Physiology*, pp-112 (2012). The disease incidence was calculated as given below:

$$\text{Disease incidence }\% = \frac{\text{Number of infected (necrotic) leaves} \times 100}{\text{Total number of leaves}}$$

Disease severity was calculated by measuring the diameter of the necrotic lesions formed in the leaves as a result of fungal infection.

The results (FIG. 3A) revealed that OsACBP5 protected against necrotrophic fungus *Alternaria brassicicola* when it was overexpressed in transgenic *Arabidopsis*. Disease assessment in both assays 7 DPI, by measuring disease incidence and disease severity following the procedures of Van de Mortel et al. *Plant Physiology*, pp-112 (2012) indicated that infection was statistically lower in the transgenic *Arabidopsis* OsACBP5-OE line, suggesting that OsACBP5 is more effective against the necrotrophic pathogen *Alternaria brassicicola* (FIG. 3B).

Example 2.3. Murashige and Skoog (MS)Plate and
Survival Assays on Transgenic *Arabidopsis* Lines
Using *Rhizoctonia solani* Show OsACBP5 Confer
Protection The root-infecting necrotroph *Rhizoctonia solani* is categorized into anastomosis groups (AG) based on their pathogenicity (Perl-Treves et al., *Molecular Plant-Microbe Interactions*, 17:70-80 (2004)) and *Rhizoctonia solani* AG-1 has been identified as the rice sheath blight-causing necrotrophic fungus which causes severe yield loss in rice cultivation world-wide (Jia et al., *Plant Disease*, 91:485-489 (2007). The necrotrophic fungal pathogen *R. solani* AG-1 was cultured onto fresh potato-dextrose agar (PDA) plates.

For MS plate assays, transgenic *Arabidopsis* seedlings transformed with 35S::AtACBP3::GFP, 35S::OsACBP5::GFP, the vector (pBI-eGFP) control and *Arabidopsis* wild-type were grown upright on the MS plates to allow roots to grow vertically on the surface media. The PDA plates with 1-week-old necrotrophic fungus *R. solani* cultures were scraped with a sterile toothpick, and each seedling were touched three times. After inoculation, the plates were sealed with plant tissue culture tape to maintain humidity and kept upright in the growth room at 22° C. with 16-h-light and 8-h-dark photoperiods (Perl-Treves et al., *Molecular Plant-Microbe Interactions*, 17:70-80 (2004)).

In the survival assays 1-week-old transgenic *Arabidopsis* seedlings transformed with 35S::AtACBP3::GFP, 35S::OsACBP5::GFP, the vector (pBI-eGFP) control and *Arabidopsis* wild-type were inoculated with necrotrophic fungal pathogen *R. solani* agar plugs in compost. Agar plugs from 2-week-old *R. solani* PDA plates were collected and mixed with the compost at the rate of 3 *R. solani* agar plugs per unit. *Arabidopsis* seeds were pre-germinated on MS plates at 22° C. with constant white light for a week and were then transplanted to the inoculated compost and grown under 22° C. with 16-h-light and 8-h-dark photoperiod (Perl-Treves et al., *Molecular Plant-Microbe Interactions*, 17:70-80 (2004)).

Disease assessment for MS plate assays carried out by measuring disease incidence as according to Van de Mortel et al. *Plant Physiology*, pp-112 (2012). The disease incidence was calculated as given below:

$$\text{Disease incidence \%} = \frac{\text{Number of infected (necrotic) leaves} \times 100}{\text{Total number of leaves}}$$

The results (FIGS. 4A, 4B) revealed that OsACBP5 protected against the necrotrophic fungus *R. solani* when it was overexpressed in transgenic *Arabidopsis*. Disease assessment in MS plate assays and survival assays, by measuring disease incidence following the procedures of Van de Mortel et al. *Plant Physiology*, pp-112 (2012) indicated that infection was statistically lower in the transgenic *Arabidopsis* OsACBP5-OE line, suggesting that OsACBP5 is more effective against the necrotrophic fungal pathogen *R. solani* (FIG. 4C).

Example 3. Electrophoretic Mobility Shift Assays (EMSAs) onW-Boxes in the OsACBP5 Promoter When the 5'-flanking region of OsACBP5 was analyzed using the PlantCARE and PLACE databases, several putative pathogen-responsive cis-elements such as the W-box (5 boxes) and MeJa responsive-element CGTCA (3 boxes), besides seed-specific Skn-1 (2 boxes) were identified (FIG. 5A). When EMSAs (Zheng et al., *Journal of Experimental Botany*, 63:2985-3000 (2012)) were used to address whether any of these boxes bind nuclear proteins from the necrotrophic fungal pathogen *Rhizoctonia solani*-infected wild-type rice leaves using a double-stranded biotin-labelled oligonucleotide probe (FIG. 5B), a W box (−1352/1348) did bind the necrotrophic fungus *R. solani*-treated (FIG. 5C, lane 2) but not untreated (FIG. 5C, lane 4) leaf nuclear extract, and a protein-DNA complex was formed (FIG. 5C, lane 2). The protein-DNA complex was no longer visible in the presence of unlabelled probe (FIG. 5C, lane 3). EMSA data (FIG. 5C) support a role for the W-box (−1352/1348) in the regulation of OsACBP5 expression by *Rhizoctonia solani*. The results from these assays suggest that the W-box (−1352/1348) which has not been previously reported in any ACBP 5' upstream region (Zheng et al., *Journal of Experimental Botany*, 63:2985-3000 (2012)) may be responsible for OsACBP5 regulation against necrotrophic fungal infection.

Example 4. *Arabidopsis* Proteins were Differentially Expressed Following Necrotrophic Fungus *Rhizoctonia solani* Infection in *Arabidopsis* OsACBP5-OEs To explore the mechanism as to why OsACBP5 overexpression resulted in tolerance to necrotrophic fungal pathogen at the translational level, proteomics analysis (sequential window acquisition of all theoretical mass spectra (SWATH)) was carried out on necrotrophic fungus *Rhizoctonia solani*-infected transgenic *Arabidopsis* OsACBP5-OE lines using the vector-transformed (pBI-eGFP) lines as control. Proteins were extracted by the trichloroacetic acid/acetone method following Wu et al., *Nature protocols*, 9: 362-374 (2014). The protein pellet was dissolved with 2 ml urea buffer (6 M urea and 4 mM calcium chloride in 200 mM 3-(N-morpholino)propanesulfonic acid (MOPS), pH 8.0) (Ross et al., *Molecular and Cellular Proteomics*, 3:1154-1169 (2004)). Equal amount of proteins (100 µg) were reduced by 10 mM dithiothreitol (DTT) and alkylated by 40 mM iodoacetamide (IAA) in the dark. After alkylation, the mixture was diluted with 4 mM $CaCl_2$ to reduce the concentration of urea to less than 2 M. Trypsin was added to digest protein at 1:20 ratio at 37° C. overnight. Following trypsin digestion, the peptides were desalted by C18 SepPak reverse-phase cartridges and performed SWATH analysis (Liang et al., *Frontiers in plant science*, 6).

Spectral, peptide, and protein identifications were analysed by ProteinPilot software. In total, 386 proteins, 1,065 peptides, and 6,514 spectrals were identified with 95% confidence in local false discovery rate (FDR). Besides, when the global FDR was applied to the whole set of data, 498 proteins, 1,614 peptides, and 9,739 spectrals were identified with 99% global FDR. Out of 498 identified proteins, 142 were significantly up-regulated in OE lines versus the vector control (pBI-eGFP) ($P<0.05$). Novel biotic stress-related proteins that were unregulated on necrotrophic fungal pathogen *R. solani* infection in OsACBP5-OE include cell wall proteins (At3g60900, At3g24480, At4g18670, At2g06850, At1g11580), proteins involved in secondary metabolism (At1g54010, At3g14210, At5g25980, At5g26000, At3g44310) and a protein involved in jasmonic acid synthesis (At3g25770) (Table 1) suggesting their potential role in conferring tolerance to necrotrophic fungal pathogens.

Example 5. Detached Leaf Assays on Transgenic OsACBP5-Overexpressing Rice (35S::OsACBP5-OE) Using *Rhizoctonia solani* Show that OsACBP5 Confers Protection The necrotrophic fungal pathogen *R. solani* AG-1 was cultured onto fresh potato-dextrose agar (PDA) plates. Rice leaves on 8-week-old plants of 35S::OsACBP5-OE, the vector (pCAMBIA1304)-transformed control and wild-type rice (ZH11) were cut into three segments, washed with distilled water thrice and were placed in a tray supported by clean glass slides at the ends so as to check them from rolling inward. Five leaves were used for each and were inoculated by placing single sclerotium of a 7-day-old PDA culture of *R. solani* in the centre of the leaf. As a control, leaf segments were inoculated with a PDA plug without hyphae. The protocol used was according to Guleria et al. (*Journal of*

*Phytopathology,* 155:654-661 (2007)). The trays with leaves were incubated in a growth chamber (25±1° C., 16 h light). The observations on lesion length around the sclerotium were recorded 3 days after inoculation.

Disease assessment for detached leaf assays were carried out by measuring disease severity as according to Van de Mortel et al. *Plant Physiology*, pp-112 (2012). Disease severity was calculated by measuring the diameter of the necrotic lesions formed in the leaves arising from fungal infection.

The results (FIG. 6A) revealed that OsACBP5 protected against the necrotrophic fungus *R. solani* when it was overexpressed in transgenic rice. Disease assessment in detached leaf assays by measuring disease severity following the procedures of Van de Mortel et al. *Plant Physiology*, pp-112 (2012) indicated that infection was statistically lower in the transgenic rice OsACBP5-OE line, suggesting that OsACBP5 was more effective in protection against the necrotrophic fungal pathogen *R. solani* (FIG. 6B).

SUMMARY

The examples demonstrate that OsACBP5 mRNA expression is induced by necrotrophic fungal pathogen infection using quantitative real time-polymerase chain reactions and EMSA. The data also shows that transgenic *Arabidopsis* overexpressing OsACBP5 (OsACBP5-OEs) are conferred improved tolerance to shoot-infecting fungal necrotrophs (*Botrytis cinerea* and *Alternaria brassicicola*) in detached leaf and whole plant assays and root-infecting fungal necrotroph *Rhizoctonia solani* in MS plate and survival assays. OsACBP5 overexpression significantly increased the survival rate of transgenic *Arabidopsis* plants exposed to necrotrophic fungal as well as biotrophic bacterial infection. In contrast AtACBP3-OEs were shown to be more susceptible than the wild-type to necrotrophic fungal pathogen *Botrytis cinerea*.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

TABLE 1

| TAIR accession | Protein name | Z-value | P-value | Functional classification |
|---|---|---|---|---|
| Cell wall proteins | | | | |
| At3g60900 | Fasciclin-like arabinogalactan-protein 10 (FLA10) | 2.4037867 | 0.022 | 10.5.1.1 cell wall.cell wall proteins.AGPs.AGP |
| At3g24480 | Leucine-rich repeat extension-like protein 4 (LRX4) | 2.965909 | 0.005 | 10.5.3 cell wall.cell wall proteins.LRR, putative disease resistance protein |
| At4g18670 | Leucine-rich repeat extensin-like protein 5 (LRX5) | 2.504201 | 0.017 | 10.5.3 cell wall.cell wall proteins.LRR |
| At2g06850 | Xyloglucan endotransglucosylase/hydrolase protein 4 (XTH4) | 2.8322113 | 0.007 | 10.7 cell wall.modification |
| At1g11580 | Pectinesterase inhibitor 18 (PME18) | 2.0758228 | 0.046 | 10.8.1 cell wall.pectin*esterases.PME |
| Proteins involved in secondary metabolism | | | | |
| At1g54010 | Myrosinase-associated protein | 2.7237568 | 0.009 | 16.5.1.3.1 secondary metabolism. sulfur-containing. glucosinolates.degradation. myrosinase |
| At3g14210 | Epithiospecifier Modifier 1 (ESM1) | 3.35275 | 0.001 | 16.5.1.3.1 secondary metabolism. sulfur-containing.glucosinolates. degradation.myrosinase |
| At5g25980 | Myrosinase 2 | 2.5899508 | 0.013 | 16.5.1.3.1.1 secondary metabolism. sulfur-containing.glucosinolates. degradation.myrosinase.TGG. Seems to function in abscisic acid (ABA) and methyl jasmonate (MeJA) signaling in guard cells. |
| At5g26000 | Myrosinase 1 | 3.3872573 | 0.001 | 16.5.1.3.1.1 secondary metabolism. sulfur-containing.glucosinolates. degradation.myrosinase.TGG. Seems to function in abscisic acid (ABA) and methyl jasmonate (MeJA) signaling in guard cells. |
| At3g44310 | Nitrilase 1 (NIT1) | 3.0978303 | 0.003 | 16.5.1.3.3 secondary metabolism. sulfur-containing.glucosinolates. degradation.nitrilase |

TABLE 1-continued

| TAIR accession | Protein name | Z-value | P-value | Functional classification |
|---|---|---|---|---|
| Jasmonic acid synthesis protein | | | | |
| At3g25770 | Allene oxide cyclase 2 (AOC2) | 3.1815429 | 0.002 | 17.7.1.4 hormone metabolism. jasmonate.synthesis-degradation.allene oxidase cyclase. Involved in the production of 12-oxo-phytodienoic acid (OPDA), a precursos of jasmonic acid. |

We claim:

1. A transgenic plant genetically engineered to express a OsACBP5 polypeptide or variant thereof in an amount effective to enhance tolerance to fungal necrotrophs relative to an unmodified plant, wherein the OsACBP5 polypeptide or variant thereof comprises an amino acid sequence having at least 90% identity to SEQ ID NO: 16,
   wherein the transgenic plant is selected for having enhanced tolerance to the fungal necrotrophs.

2. The transgenic plant of claim 1, wherein the plant is of a *Brassicaceous* plant species.

3. The transgenic plant of claim 1, wherein the transgenic plant is a plant selected from the group consisting of a tomato, a grain crop and a cotton plant.

4. The transgenic plant of claim 1, wherein the OsACBP5 polypeptide or variant thereof comprise the amino acid sequence of SEQ ID NO:16.

5. A seed that produces the transgenic plant of claim 1.

6. A transgenic plant cell or plant part of the transgenic plant of claim 1.

7. A method of obtaining enhanced tolerance to fungal necrotrophs in a plant or plant cell comprising:
   genetically engineering the plant or plant cell to express a OsACBP5 polypeptide or variant thereof; and
   selecting the plant or plant cell for having enhanced tolerance to the fungal necrotrophs relative to a non-genetically engineered plant,
   wherein the OsACBP5 polypeptide or variant thereof comprises an amino acid sequence having at least 90% identity to SEQ ID NO:16.

8. The method of claim 7, wherein the plant or plant cell is of a *Brassicaceous* plant species.

9. The method of claim 8, wherein the plant or plant cell is a grain crop cell.

10. The method of claim 8 wherein the plant or plant cell is from a plant selected from the group consisting of a tomato, a cotton and a rice plant.

11. The method of claim 8, wherein the OsACBP5 polypeptide or variant thereof comprise the amino acid sequence of SEQ ID NO:16.

12. A method of obtaining a plant part having tolerance to fungal necrotrophs, comprising:

obtaining a plant part genetically modified to express a OsACBP5 polypeptide or variant thereof;
growing the plant part under conditions where it is exposed to fungal necrotrophs stress that is growth-inhibiting to a plant of the same type not genetically modified to express said OsACBP5; and
selecting the plant part for having enhanced tolerance to the fungal necrotrophs relative to the plant of the same type not genetically modified to express said OsACBP5,
wherein the OsACBP5 polypeptide or variant thereof comprises an amino acid sequence having at least 90% identity to SEQ ID NO:16.

13. The method of claim 12, wherein obtaining the plant part comprises growing the plant part from a seed or obtaining a plant cutting.

14. The method of claim 12, wherein the plant part is comprised in a plant.

15. The method of claim 12, wherein the fungal stress is measured by the ability to survive fungal infection.

16. A method of screening for functional OsACBP5 variants, comprising: obtaining a cell genetically modified to express a candidate OsACBP5 variant; growing the cell under conditions of fungal stress that is growth-inhibiting to a native cell of the same type; observing whether the cell exhibits a reduction in growth inhibition; and, if so, identifying the candidate OsACBP5 variant as functional.

17. The method of claim 16, further comprising regenerating the genetically modified cell containing the functional OsACBP5 variant into a plant.

18. The method of claim 17, further comprising obtaining progeny of said plant that comprise cells expressing the functional OsACBP5 variant.

19. The transgenic plant of claim 1, wherein the fungal necrotrophs are selected from the group consisting of *Rhizoctonia solani, Botrytis cinerea*, and *Alternaria brassicicola*.

20. The method of claim 7, wherein the fungal necrotrophs are selected from the group consisting of *Rhizoctonia solani, Botrytis cinerea*, and *Alternaria brassicicola*.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: artificial
<220> FEATURE:
<223> OTHER INFORMATION: primers for PCR

<400> SEQUENCE: 1
aggccgtcct ctctctgtat        20

<210> SEQ ID NO 2
<211> LENGTH: 20
<212> TYPE: DNA
<213> ORGANISM: artificial
<220> FEATURE:
<223> OTHER INFORMATION: primer

<400> SEQUENCE: 2
ggggagagca tatccttcat        20

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
tgtcaatact gctcgtcctg        20

<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4
tagtcgctca ttgcttcctc        20

<210> SEQ ID NO 5
<211> LENGTH: 21
<212> TYPE: DNA
<213> ORGANISM: artificial
<220> FEATURE:
<223> OTHER INFORMATION: primer

<400> SEQUENCE: 5
atgggtttgc aggaggagtt t        21

```
<210> SEQ ID NO 6
<211> LENGTH: 21
<212> TYPE: DNA
<213> ORGANISM: artificial
<220> FEATURE:
<223> OTHER INFORMATION: primer

<400> SEQUENCE: 6
ctgcttgtag aggccataga g                                              21

<210> SEQ ID NO 7
<211> LENGTH: 21
<212> TYPE: DNA
<213> ORGANISM: artificial
<220> FEATURE:
<223> OTHER INFORMATION: primer

<400> SEQUENCE: 7
tgggtctgca ggaggatttt g                                              21

<210> SEQ ID NO 8
<211> LENGTH: 21
<212> TYPE: DNA
<213> ORGANISM: artificial
<220> FEATURE:
<223> OTHER INFORMATION: primer

<400> SEQUENCE: 8
acggtggcct gcttgtagag t                                              21

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9
gcatctggct gctggtgtag                                                20

<210> SEQ ID NO 10
<211> LENGTH: 22
<212> TYPE: DNA
<213> ORGANISM: artificial
<220> FEATURE:
<223> OTHER INFORMATION: primer

<400> SEQUENCE: 10
gcatttgcat tgacaagaat ct                                             22

<210> SEQ ID NO 11
<211> LENGTH: 20
<212> TYPE: DNA
<213> ORGANISM: artificial
<220> FEATURE:
<223> OTHER INFORMATION: primer

<400> SEQUENCE: 11
gaggctattc caggatggat                                                20

<210> SEQ ID NO 12
<211> LENGTH: 22
<212> TYPE: DNA
<213> ORGANISM: artificial
<220> FEATURE:
<223> OTHER INFORMATION: primer
```

<400> SEQUENCE: 12
ctgtcatgtt ggttgattgt at    22

<210> SEQ ID NO 13
<211> LENGTH: 20
<212> TYPE: DNA
<213> ORGANISM: artificial
<220> FEATURE:
<223> OTHER INFORMATION: primer

<400> SEQUENCE: 13
ggtggtggca ataacaaaag    20

<210> SEQ ID NO 14
<211> LENGTH: 19
<212> TYPE: DNA
<213> ORGANISM: artificial
<220> FEATURE:
<223> OTHER INFORMATION: primer

<400> SEQUENCE: 14
gcaaggggaa cacgacctt    19

<210> SEQ ID NO 15
<211> LENGTH: 2207
<212> TYPE: DNA
<213> ORGANISM: Oryza sativa

<400> SEQUENCE: 15

```
ggttgctcga tcgtctcgct ctcctctcct cttctcttcg tctctcctcc tgacccttt    60
tccgctttcc cttttccccc ctcctcgatc cgcggcgcaa ccgaacacga aagcgagaga   120
gagaggagtg cagccgctgc cctgtcccct caccgcgccg cgccgacatg gagctgttct   180
acgagctgct cctcacggcg gctgcctccc tcctcgtcgc cttcctgctg gccaggctgc   240
tggcctccgc cgccaccgcc agtgatcccc gccgccgcgc gcccgatcac gccgccgtga   300
tcgcggagga ggaggcggtg gtggtggagg aggagaggat catcgaggtc gatgaggtcg   360
aggtgaagag cgcgcgcgcg agggagtgcg tggtttcgga ggggtgggtc gaggtgggga   420
gggcctcgtc ggcggagggg aagctcgagt gcttgccgga ggaagaggag gctcccgcga   480
aggccgctcg ggagcttgtt ctcgatgccg ttttggagga acgcgaggag gaaggacaag   540
ttggcgaaga gcggtgcgat ttggccgctg cggtggcgga ggtcgtggga gtgaagccgc   600
atgagttggg ggttgaagct gctcccgggg aggtatctga cgtgacgctg gaggaaggga   660
aggtgcagga tgttggggtg gagcagcatg atttggtcgc cgaggctgct ccaagggaag   720
ctcttgacac agggttggag aaacaggtg ttcccatcat tgaagcggtt gaaatcaagc   780
ggcaggatga tctgggtgct gaggtagctc cgagtgacgt tcctgaggtg aatttgagc   840
aacagggagt tcgcattatt gaagctattg atgtgaatca acatcatcgg ttgctctgg   900
ctgctcctgc ggaagttgtt gatgcgggat tggaggagag ggtccaagct attgaagcag   960
ggtcatctgg attgacttcc gagacagttc ctgaagaggt tcttgacgag ttatctgaga  1020
agcaagaaga gcaagttatt gaagagaagg aacatcaatt ggctgcagcg actgctccag  1080
tagcaattcc tggtgtggca ttggcagaga cggaggaact aaagaagaa caatcctctg  1140
aaaaagctgt caatgttcat gaagaagttc agagtaagga cgaagctaaa tgcaagctcc  1200
atctggttga tcaacaagaa ggttcggctt ctaaggtgga gctggtgggg aggaataccg  1260
acaatgtgga aattagccat ggaagcagtt ctggtgacaa aatgattgct gagttgaccg  1320
```

-continued

```
aggaggaatt gacattgcaa ggtgtgcccg cagatgagac tcagacagac atggaatttg    1380
gggagtggga agggattgaa agaactgaga tagaaaagag gtttggtgtg gcagcagcgt    1440
ttgcatctag tgacgccggg atggctgccc tgtcaaagct tgatagtgat gtgcagctgc    1500
agctgcaggg actccttaag gttgccattg atggtccatg ctatgactct acacagccac    1560
ttaccttgag gccttcatct cgtgcaaaat gggctgcttg gcaaaagcta gggaacatgt    1620
atccggagac agctatggaa agatacatga atcttttgtc agaggctatt ccaggatgga    1680
tgggtgacaa tatctcgggc acaaaggaac atgaagctgg tgatgatgct gtagggtctg    1740
tcttaacaat gacttcaaat acaatcaacc aacatgacag tcaagggaat gaagacaata    1800
ctggcatgta tgaaggtcac ttgacaagtt cccctaaccc agaaaaggac agagttctga    1860
catccctgct gaggtgaatg aacataacac tcatggaaga tttcttgcat cagtgatttc    1920
agcccattgc tgagaccgct accgatgcct tcctcataag attagatttg tacagtgctc    1980
ctgtggtgct aatattagtg ttgtcatggt gttggtttgt gtatatatat gactgtatat    2040
atcagtaact gccggtccta ctgcgtgtat tccgccagca gcagacttat catctggtat    2100
tctggtgtag tctgtagaac aatacatctg gtgagtcgta attatatgtc gatacgatgc    2160
agtttggaag gagaaattga agtggttgga aaaccagttg aaaggac                  2207
```

<210> SEQ ID NO 16
<211> LENGTH: 569
<212> TYPE: PRT
<213> ORGANISM: Oryza sativa

<400> SEQUENCE: 16

```
Met Glu Leu Phe Tyr Glu Leu Leu Thr Ala Ala Ser Leu Leu
1               5                   10                  15

Val Ala Phe Leu Leu Ala Arg Leu Leu Ala Ser Ala Ala Thr Ala Ser
                20                  25                  30

Asp Pro Arg Arg Arg Ala Pro Asp His Ala Ala Val Ile Ala Glu Glu
            35                  40                  45

Glu Ala Val Val Val Glu Glu Glu Arg Ile Ile Glu Val Asp Glu Val
        50                  55                  60

Glu Val Lys Ser Ala Arg Ala Arg Glu Cys Val Val Ser Glu Gly Trp
65                  70                  75                  80

Val Glu Val Gly Arg Ala Ser Ser Ala Glu Gly Lys Leu Glu Cys Leu
                85                  90                  95

Pro Glu Glu Glu Glu Ala Pro Ala Lys Ala Ala Arg Glu Leu Val Leu
            100                 105                 110

Asp Ala Val Leu Glu Glu Arg Glu Glu Gly Gln Val Gly Glu Glu
        115                 120                 125

Arg Cys Asp Leu Ala Ala Ala Val Ala Glu Val Val Gly Val Lys Pro
    130                 135                 140

His Glu Leu Gly Val Glu Ala Ala Pro Gly Glu Val Ser Asp Val Thr
145                 150                 155                 160

Leu Glu Glu Gly Lys Val Gln Asp Val Gly Val Glu Gln His Asp Leu
                165                 170                 175

Val Ala Glu Ala Ala Pro Arg Glu Ala Leu Asp Thr Gly Leu Glu Lys
            180                 185                 190

Gln Gly Val Pro Ile Ile Glu Ala Val Glu Ile Lys Arg Gln Asp Asp
        195                 200                 205

Leu Gly Ala Glu Val Ala Pro Ser Asp Val Pro Glu Val Glu Phe Glu
```

210                 215                 220
Gln Gln Gly Val Arg Ile Ile Glu Ala Ile Asp Val Asn Gln His His
225                 230                 235                 240

Arg Val Ala Leu Ala Pro Ala Glu Val Asp Ala Gly Leu Glu
                245                 250                 255

Glu Arg Val Gln Ala Ile Glu Ala Gly Ser Ser Gly Leu Thr Ser Glu
                260                 265                 270

Thr Val Pro Glu Glu Val Leu Asp Glu Leu Ser Glu Lys Gln Glu Glu
                275                 280                 285

Gln Val Ile Glu Glu Lys Glu His Gln Leu Ala Ala Thr Ala Pro
290                 295                 300

Val Ala Ile Pro Gly Val Ala Leu Ala Glu Thr Glu Glu Leu Lys Glu
305                 310                 315                 320

Glu Gln Ser Ser Glu Lys Ala Val Asn Val His Glu Glu Val Gln Ser
                325                 330                 335

Lys Asp Glu Ala Lys Cys Lys Leu His Leu Val Asp Gln Gln Glu Gly
                340                 345                 350

Ser Ala Ser Lys Val Glu Leu Val Gly Arg Asn Thr Asp Asn Val Glu
                355                 360                 365

Ile Ser His Gly Ser Ser Ser Gly Asp Lys Met Ile Ala Glu Leu Thr
370                 375                 380

Glu Glu Glu Leu Thr Leu Gln Gly Val Pro Ala Asp Glu Thr Gln Thr
385                 390                 395                 400

Asp Met Glu Phe Gly Glu Trp Glu Gly Ile Glu Arg Thr Glu Ile Glu
                405                 410                 415

Lys Arg Phe Gly Val Ala Ala Phe Ala Ser Ser Asp Ala Gly Met
                420                 425                 430

Ala Ala Leu Ser Lys Leu Asp Ser Asp Val Gln Leu Gln Leu Gln Gly
                435                 440                 445

Leu Leu Lys Val Ala Ile Asp Gly Pro Cys Tyr Asp Ser Thr Gln Pro
450                 455                 460

Leu Thr Leu Arg Pro Ser Ser Arg Ala Lys Trp Ala Ala Trp Gln Lys
465                 470                 475                 480

Leu Gly Asn Met Tyr Pro Glu Thr Ala Met Glu Arg Tyr Met Asn Leu
                485                 490                 495

Leu Ser Glu Ala Ile Pro Gly Trp Met Gly Asp Asn Ile Ser Gly Thr
                500                 505                 510

Lys Glu His Glu Ala Gly Asp Asp Ala Val Gly Ser Val Leu Thr Met
                515                 520                 525

Thr Ser Asn Thr Ile Asn Gln His Asp Ser Gln Gly Asn Glu Asp Asn
530                 535                 540

Thr Gly Met Tyr Glu Gly His Leu Thr Ser Ser Pro Asn Pro Glu Lys
545                 550                 555                 560

Gly Gln Ser Ser Asp Ile Pro Ala Glu
                565

<210> SEQ ID NO 17
<211> LENGTH: 41
<212> TYPE: DNA
<213> ORGANISM: Artificial sequence
<220> FEATURE:
<223> OTHER INFORMATION: Primer

<400> SEQUENCE: 17
tgtaccacat gggtgtcatg gcggaggtag gtgggcggcg g        41

```
<210> SEQ ID NO 18
<211> LENGTH: 41
<212> TYPE: DNA
<213> ORGANISM: Artificial sequence
<220> FEATURE:
<223> OTHER INFORMATION: Primer

<400> SEQUENCE: 18
ccgccgccca cctacctccg ccatgacacc catgtggtac a                41
```

UNITED STATES PATENT AND TRADEMARK OFFICE
CERTIFICATE OF CORRECTION

PATENT NO. : 10,968,463 B2
APPLICATION NO. : 16/313375
DATED : April 6, 2021
INVENTOR(S) : Mee Len Chye It is certified that error appears in the above-identified patent and that said Letters Patent is hereby corrected as shown below:

On the Title Page

Item [54], and in the Specification, Column 1, Lines 1-5, please delete "Methods of Using Acyl-Coenzymea-Binding Proteins to Enhance Tolerance to Necrotrophic Fungal Pathogens in Genetically Modified Plants" and insert -- Methods of Using Acyl-Coenzyme A-Binding Proteins to Enhance Tolerance to Necrotrophic Fungal Pathogens in Genetically Modified Plants --

Signed and Sealed this
Fifteenth Day of August, 2023

Katherine Kelly Vidal
*Director of the United States Patent and Trademark Office*